US008367334B2

(12) United States Patent
Pugh et al.

(10) Patent No.: US 8,367,334 B2
(45) Date of Patent: Feb. 5, 2013

(54) METHODS, SYSTEMS AND KITS FOR DETECTING PROTEIN-NUCLEIC ACID INTERACTIONS

(75) Inventors: Benjamin Franklin Pugh, State College, PA (US); Ho Sung Rhee, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 150 days.

(21) Appl. No.: 12/817,027

(22) Filed: Jun. 16, 2010

(65) Prior Publication Data
US 2010/0323361 A1 Dec. 23, 2010

Related U.S. Application Data

(60) Provisional application No. 61/218,290, filed on Jun. 18, 2009.

(51) Int. Cl.
*C12Q 1/68* (2006.01)
*G01N 33/53* (2006.01)
*C12P 19/34* (2006.01)
*C07H 21/02* (2006.01)
*C07K 1/00* (2006.01)

(52) U.S. Cl. ........ 435/6.1; 611/6.12; 611/7.1; 611/91.1; 611/91.2; 536/23.1; 530/350

(58) Field of Classification Search .................... 435/6.1, 435/6.11, 6.12, 91.1, 91.2, 283.1, 287.1, 435/287.2; 436/94, 501; 536/23.1, 24.3, 536/24.33, 25.3; 530/300, 350
See application file for complete search history.

(56) References Cited

U.S. PATENT DOCUMENTS

| 5,807,522 A | 9/1998 | Brown et al. |
| 5,837,832 A | 11/1998 | Chee et al. |
| 2008/0241822 A1 | 10/2008 | Wyrick et al. |

FOREIGN PATENT DOCUMENTS

WO 95/11995 A1 5/1995

OTHER PUBLICATIONS

"chromatin" from Wikipedia, the free encyclopedia. Printed on May 17, 2012.*
The definition of "genome". Printed on May 17, 2012.*
"exonuclease" from Wikipedia, the free encyclopedia. Printed on May 17, 2012.*
Abdurashidova, G. et al. (2003) "Localization of proteins bound to a replication origin of human DNA along the cell cycle," The EMBO Journal, 22(16): 4294-4303.
Meyer, P.R. et al. (2007) "Stable Complexes Formed by HIV-1 Reverse Transcriptase at Distinct Positions on the Primer-Template Controlled by Binding Deoxynucleoside Triphosphates or Foscarnet," J. Mol. Biol. 369(1): 41-54.
Struhl, K. (1995) "Yeast Transcriptional Regulatory Mechanisms," Annu. Rev. Genetics, 29: 651-674.

(Continued)

*Primary Examiner* — Frank W Lu
(74) *Attorney, Agent, or Firm* — Novak Druce Connolly Bove & Quigg LLP

(57) ABSTRACT

Methods, systems and kits for detecting protein-nucleic acid interactions, in particular, detecting the genomic location to near-base pair resolution at which a particular protein (e.g., transcription factor) binds includes combining steps of a conventional chromatin immunoprecipitation (ChIP) assay with use of an exonuclease that digests nucleic acid strands in the 5'-3' or 3'-5' direction until it reaches a bound protein including a protein crosslinked to the nucleic acid. Proteins that inefficiently crosslink to a nucleic acid and thus are very difficult to detect, are expected to be significantly detected by the kits and methods described herein.

23 Claims, 19 Drawing Sheets

OTHER PUBLICATIONS

Ptashne, M. et al. (1997) "Transcriptional activation by recruitment," Nature, 386: 569-577.

Lee, T.I. et al. (2002) "Transcriptional Regulatory Networks in *Saccharomyces cerevisiae*," Science, 298: 799-804.

Solomon, M.J. et al. (1988) "Mapping Protein-DNA Interactions in Vivo with Formaldehyde: Evidence That Histone H4 is Retained on a Highly Transcribed Gene," Cell, 53: 937-947.

Hecht, A. et al. (1996) "Spreading of transcriptional repressor SIR3 from telomeric heterochromatin," Nature, 383: 92-96.

Ren, B. et al. (2000) "Genome-Wide Location and Function of DNA Binding Proteins," Science, 290: 2306-2309.

Albert, I. et al. (2007) "Translational and rotational settings of H2A.Z nucleosomes across the *Saccharomyces cerevisiae* genome," Nature, 446: 572-576.

Johnson, D.S. et al. (2007) "Genome-Wide Mapping of in Vivo Protein-DNA Interactions," Science, 316: 1497-1502.

Robertson, G. et al. (2007) "Genome-wide profiles of STAT1 DNA association using chromatin immunoprecipitation and massively parallel sequencing," Nature Methods, 4(8): 651-657.

Jothi, R. et al. (2008) "Genome-wide identification of in vivo protein-DNA binding sites from ChIP-Seq data," Nucleic Acids Research, 36(16): 5221-5231.

Valouev, A. et al. (2008) "Genome-wide analysis of transcription factor binding sites based on ChIP-Seq data," Nature Methods, 5(9): 829-834.

Badis, G. et al. (2009) "Diversity and Complexity in DNA Recognition by Transcription Factors," Science, 324: 1720-1723.

Hesselberth, J.R. et al. (2009) "Global mapping of protein-DNA interactions in vivo by digital genomic footprinting," Nature Methods, 6(4): 283-289.

Rozowsky, J. et al. (2009) "PeakSeq enables systematic scoring of ChIP-seq experiments relative to controls," Nature Biotechnology, 27(1): 66-75.

Peng, S. et al. (2007) "Normalization and experimental design for ChIP-chip data," BMC Bioinformatics, 8: 219.

Tuteja, G. et al. (2009) "Extracting transcription factor targets from ChIP-Seq data," Nucleic Acids Research, 37(17): e113.

Solomon, M.J. et al. (1985) "Formaldehyde-mediated DNA-protein crosslinking: A probe for in vivo chromatin structures," Proc. Natl. Acad. Sci. USA, 82: 6470-6474.

Orlando, V. (2000) "Mapping chromosomal proteins in vivo by formaldehyde-crosslinked-chromatin immunoprecipitation," Trends Biochem. Sci., 25: 99-104.

Koerber, R.T. et al. (2009) "Interaction of Transcriptional Regulators with Specific Nucleosomes across the *Saccharomyces* Genome," Molecular Cell, 35: 889-902.

Morrow, B.E. et al. (1989) "Proteins That Bind to the Yeast rDNA Enhancer," The Journal of Biological Chemistry, 264(15): 9061-9068.

Harbison, C.T. et al. (2004) "Transcriptional regulatory code of a eukaryotic genome," Nature, 431: 99-104.

Venters, B.J. et al. (2009) "A canonical promoter organization of the transcription machinery and its regulators in the *Saccharomyces* genome," Genome Research, 19: 1-12.

Albert, I. et al. (2008) "GeneTrack-a genomic data processing and visualization framework," Bioinformatics, 24(10): 1305-1306.

Kulkens, T. et al. (1992) "A system to study transcription by yeast RNA polymerase I within the chromosomal context: functional analysis of the ribosomal DNA enhancer and the RBP1/REB1 binding sites," The EMBO Journal, 11(12): 4665-4674.

Wang, K.L. et al. (1998) "Positive and Negative Autoregulation of REB1 Transcription in *Saccharomyces cerevisiae*," Molecular and Cellular Biology, 18(7): 4368-4376.

Biswas, S. et al. (2008) "Mechanistic Insights into Replication Termination as Revealed by Investigations of the Reb1-Ter3 Complex of *Schizosaccharomyces pombe*," Molecular and Cellular Biology, 28(22): 6844-6857.

Hartley, P.D. et al. (2009) "Mechanisms that Specify Promoter Nucleosome Location and Identity," Cell, 137: 445-458.

Mitsis, P.G. et al. (1999) "Characterization of the interaction of lambda exonuclease with the ends of DNA," Nucleic Acids Research, 27(15): 3057-3063.

Subramanian, K. et al. (2003) "The enzymatic basis of processivity in a exonuclease," Nucleic Acids Research, 31(6): 1585-1596.

Bailey, T.L. et al. (2006) "MEME: discovering and analyzing DNA and protein sequence motifs," Nucleic Acids Research, 34: W369-W373.

Kim, J. et al. (2005) "Mapping DNA-protein interactions in large genomes by sequence tag analysis of genomic enrichment," Nature Methods, 2(1): 47-53.

Chen, J. et al. (2005) "Identification of the mismatch repair genes PMS2 and MLH1 as p53 target genes by using serial analysis of binding elements," Proc. Natl. Acad. Sci. USA, 102(13): 4813-4818.

Bhinge, A.A. et al. (2007) "Mapping the chromosomal targets of STAT1 by Sequence Tag Analysis of Genomic Enrichment (Stage)," Genome Research, 17: 910-916.

Lockhart, D.J. et al. (1996) "Expression monitoring by hybridization to high-density oligonucleotide arrays," Nature Biotechnology, 14: 1675-1680.

Schena, M. et al. (1996) "Parallel human genome analysis: Microarray-based expression monitoring of 1000 genes," Proc. Natl. Acad. Sci. USA, 93: 10614-10619.

Pugh, B.F. et al. (2001) "Genome-wide analysis of protein-DNA interactions in living cells," Biology, 2(4): 1013.1-1013.3.

Lee, T.I. et al. (2006) "Chromatin immunoprecipitation and microarray-based analysis of protein location," Nature Protocols, 1(2): 729-748.

Collas, P. et al. (2008) "Chop it, ChIP it, check it: the current status of chromatim immunoprecipitation", Frontiers in Bioscience, 13: 922-943.

Ngoc, L.B.T. et al. (2008) "Ligation-mediated PCR, a fast and reliable technique for insertion sequence-based typing of *Xanthomonas citri* pv.citri", FEMS Microbiol. Lett., vol. 288: 33-39.

Tagoh, H. et al. (2006) "In Vivo Genomic Footprinting Using LM—PCR Methods", Methods in Molecular Biology, vol. 325: 285-314.

Rhee et al., "Comprehensive Genome-wide Protein-DNA Interactions Detected at Single-Nucleotide Resolution," Cell, Dec. 9, 2011; 9, pp. 1408-1419.

European Patent Office Communication including Supplementary European Search Report (European Application No. 10790137.3), dated Sep. 27, 2012, 6 pages.

* cited by examiner

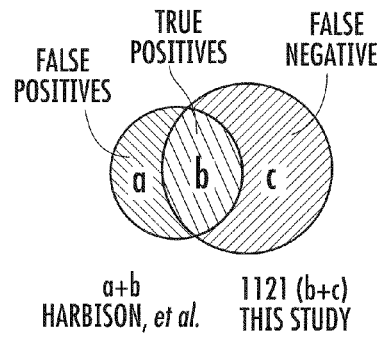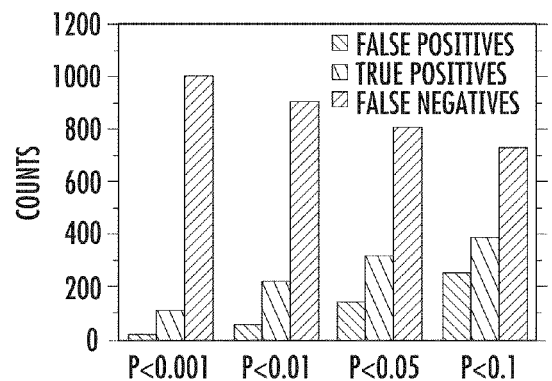
FIG. 8A
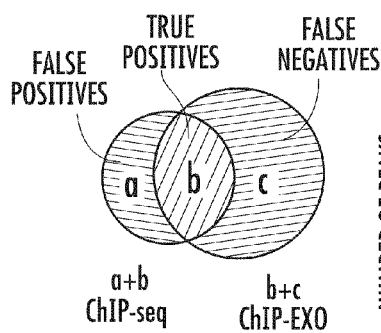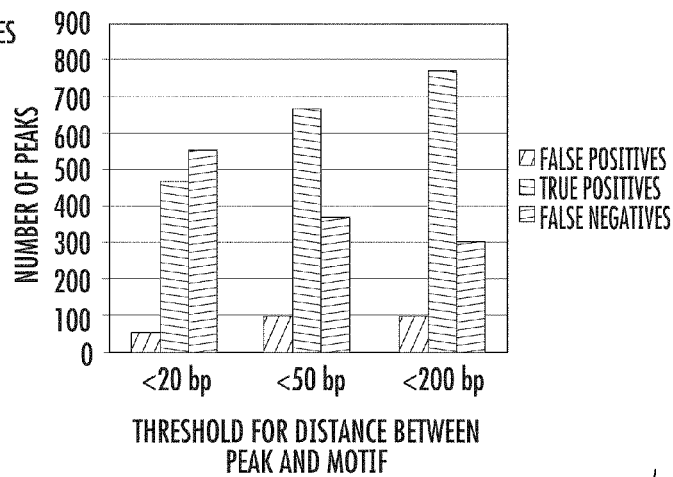
FIG. 8B

| | Sample information | | | Experiment information | | | Analysis methods |
|---|---|---|---|---|---|---|---|
| | Factor | Class | Species | Amount of cells | Purification | Resin | (Binding site size)/2 |
| 1 | Reb1 | Sequence-specific factor | S. cerevisiae (yeast) | 250 ml | TAP-tag | IgG sepharose | 14bp |
| 2 | Rap1 | Sequence-specific factor | S. cerevisiae | 250 ml | TAP-tag | IgG sepharose | 13bp |
| 3 | Gal4 | Sequence-specific factor | S. cerevisiae | 500 ml | TAP-tag | IgG sepharose | 9bp |
| 4 | Ume6 | Sequence-specific factor | S. cerevisiae | 250 ml | TAP-tag | IgG sepharose | 12bp |
| 5 | Sok2 | Sequence-specific factor | S. cerevisiae | 250 ml | TAP-tag | IgG sepharose | 9bp |
| 6 | Phd1 | Sequence-specific factor | S. cerevisiae | 250 ml | TAP-tag | IgG sepharose | 12bp |
| 7 | Put3 | Sequence-specific factor | S. cerevisiae | 250 ml | TAP-tag | IgG sepharose | 9bp |
| 8 | Sua7 | General transcription factor | S. cerevisiae | 250 ml | TAP-tag | IgG sepharose | 8bp |
| 9 | Taf1 | General transcription factor | S. cerevisiae | 250 ml | TAP-tag | IgG sepharose | 15bp |
| 10 | Ssl2 | General transcription factor | S. cerevisiae | 250 ml | TAP-tag | IgG sepharose | 20bp |
| 11 | Rpo21 | General transcription factor | S. cerevisiae | 250 ml | TAP-tag | IgG sepharose | 6bp |
| 12 | Toa2 | General transcription factor | S. cerevisiae | 500 ml | TAP-tag | IgG sepharose | 18bp |
| 13 | Htz1 | Histone variant | S. cerevisiae | 250 ml | TAP-tag | IgG sepharose | 8bp |
| 14 | Hta2 | Histone subunit | S. cerevisiae | 500 ml | TAP-tag | IgG sepharose | 7bp |
| 15 | Htb1 | Histone subunit | S. cerevisiae | 500 ml | TAP-tag | IgG sepharose | 7bp |
| 16 | H3K4me3 | Histone modification | S. cerevisiae | 250 ml | Antibody | Protein A sepharose | 8bp |
| 17 | GAGA | Sequence-specific factor | D. melanogaster (fly) | 6 x 10⁶ | Antibody | Protein A sepharose | 22bp |
| 18 | Rpb3 | General transcription factor | D. melanogaster | 6 x 10⁶ | Antibody | Protein A sepharose | Not determined |
| 19 | CTCF | Sequence-specific factor | Homo sapiens (human) | 3 x 10⁶ | Antibody | Protein A sepharose | Not determined |
| 20 | p53 | Sequence-specific factor | Homo sapiens | 3 x 10⁶ | Antibody | Protein A sepharose | Not determined |

FIG. 10

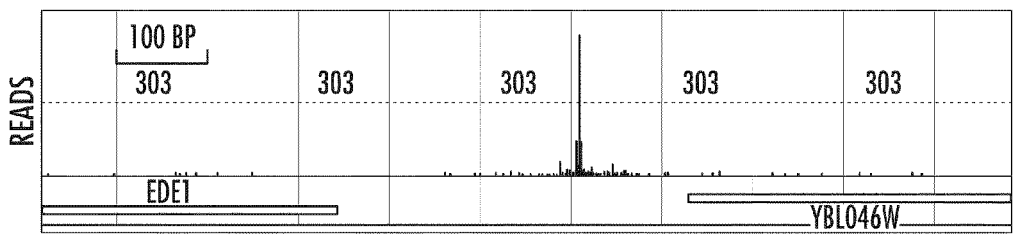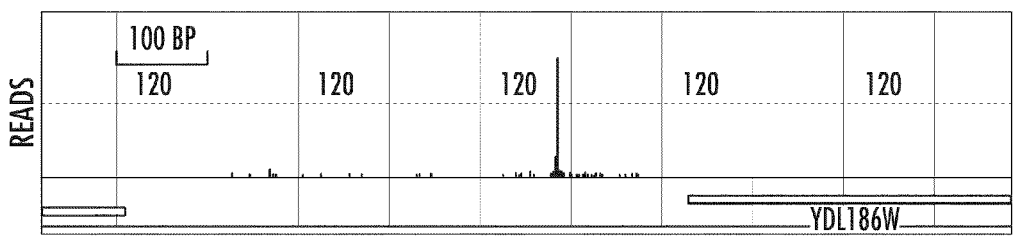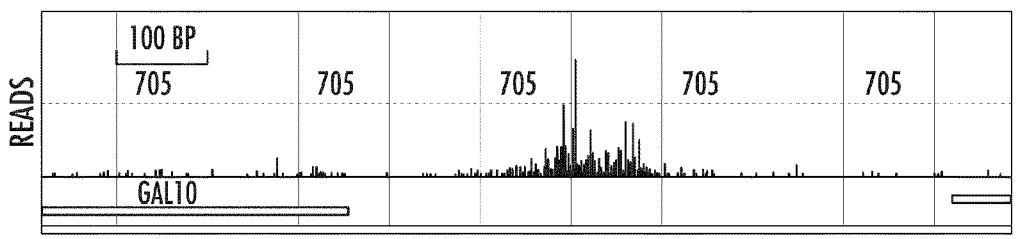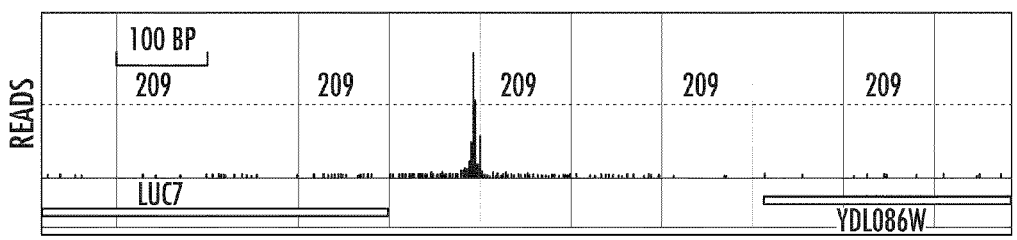
FIG. 11

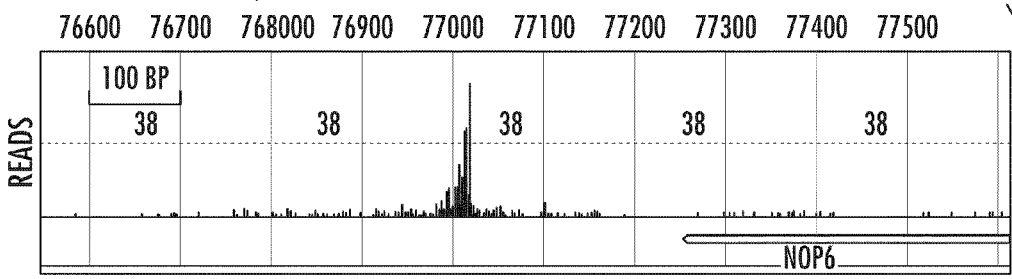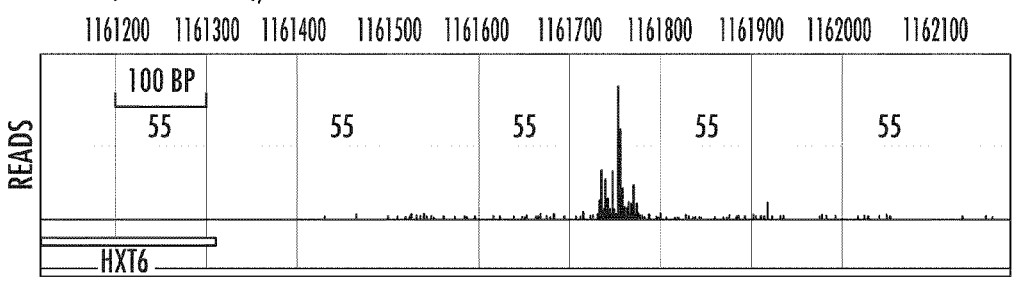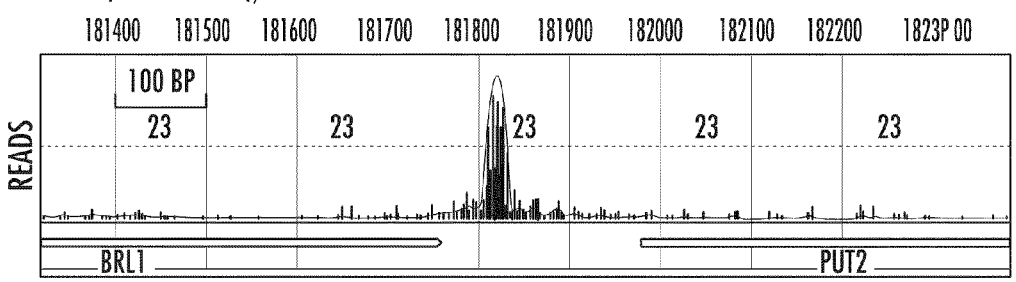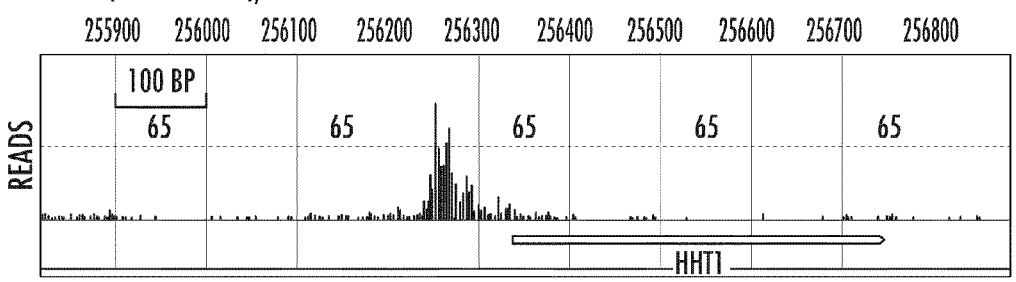
FIG. 12

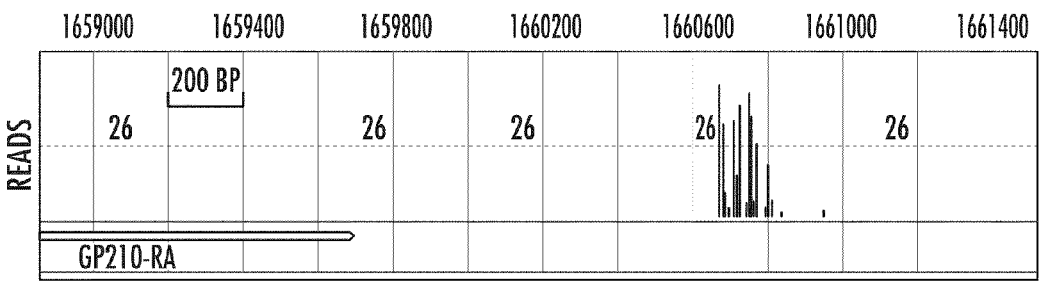
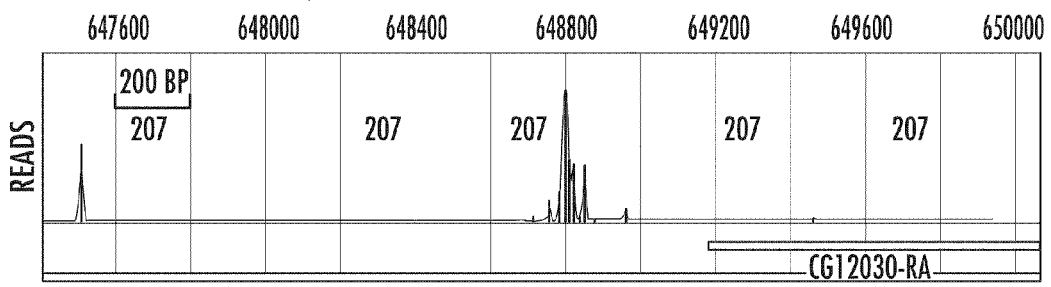
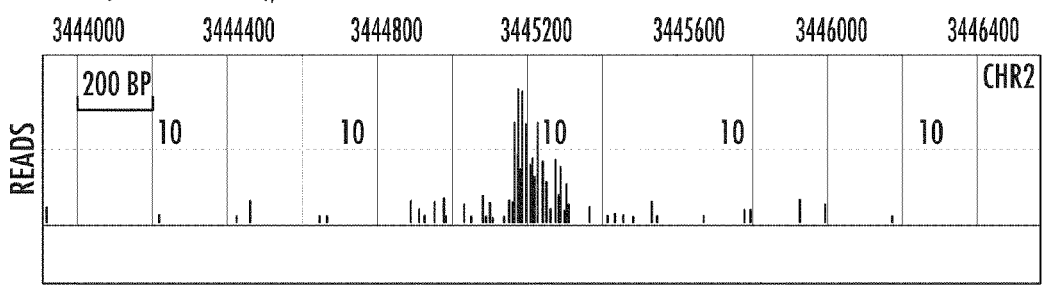
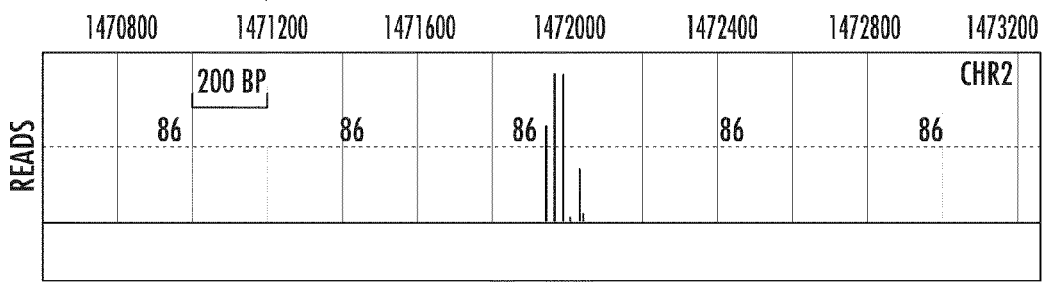
FIG. 15

US 8,367,334 B2

METHODS, SYSTEMS AND KITS FOR DETECTING PROTEIN-NUCLEIC ACID INTERACTIONS

CROSS-REFERENCE TO RELATED APPLICATIONS

This application claims the benefit of Provisional Application Ser. No. 61/218,290 filed Jun. 18, 2009, which is herein incorporated by reference in its entirety.

FEDERALLY SPONSORED RESEARCH

This invention was made with government support under grant no. 5R01ES013768 awarded by The National Institutes of Health. The U.S. government has certain rights in the invention.

FIELD OF THE INVENTION

The invention relates generally to the fields of molecular genetics and molecular biology.

BACKGROUND

Eukaryotic genes are regulated by sequence-specific DNA-binding proteins. These factors interact with other proteins to modify and remodel resident chromatin, and ultimately promote the assembly of the transcription pre-initiation complex (PIC) that includes RNA polymerase II and its associated elongation factors. In Saccharomyces cerevisiae, over 400 proteins are involved in some aspect of gene regulation. In vertebrates, this number increases by an order of magnitude.

Each of the hundreds of gene regulatory proteins has a function, and that function depends on its precise location in the genome. For example, nucleosomes package DNA and control its accessibility. A TATA box, which binds TBP and promotes PIC assembly, may be located just inside the nucleosome border where it is sequestered and thus unable to promote PIC assembly. Movement of the nucleosome by as little as 5 by has been shown to promote TATA box utilization in yeast. In higher eukaryotes, the stereospecific arrangement of proteins in an enhancesome is critical for its function. Repositioning of its DNA binding components by a few base pair (bp) changes the rotational setting of the components on the DNA helical surface, resulting in nonfunctional complexes. Knowing the exact position of proteins to near single base-pair resolution provides mechanistic information on how proteins work together to regulate gene expression.

Other types of genomic location information are also quite valuable, and perhaps of more widespread interest. For example, knowing which gene (or promoter region) a regulatory protein binds to provides information about the repertoire of genes that a protein might regulate. Knowing which transcription factors bind to which genes and exactly where they bind is critical in understanding how genes are misregulated in human diseases. To this day, it remains largely unknown precisely where gene regulatory proteins are bound throughout a genome.

Chromatin immunoprecipitation (ChIP) has been one of the most widely used assays to measure the occupancy of a protein to a particular genomic location in vivo. This method, however, is associated with several drawbacks. For example, the experimenter is required to know, within a few hundred bp, where the protein is bound in the genome, in that specific primers need to be designed to interrogate that position. In 2000, a technological advancement was made—the development of ChIP-chip. Rather than having to know a priori where a factor might bind, DNA microarray technology allowed virtually an entire genome to be queried (reviewed by Pugh and Gilmour, Genome vol. 2 REVIEWS 1013.Epub, 2001). In essence, the identity of the bound DNA could be identified by its ability to hybridize to an array of pre-defined genomic sequences or probes. Early microarrays consisted of long PCR-generated probes that spanned intergenic regions (in compact genomes like yeast). Later microarrays consisted of oligonucleotides that have been uniformly tiled across an entire genome. Microarray-based ChIP-chip procedures, however, have no mechanism to map individual molecules, and instead measure bulk behavior of populations of DNA molecules.

ChIP-chip is now being replaced by ChIP-seq, where instead of using microarrays to identify the bound DNA, each bound DNA molecule is sequenced. This provides a much more stringent sequence identification than the DNA hybridization approach of microarrays, which can be confounded by cross-hybridization of similar sequences. Early ChIP-seq experiments were limited by the number of sequencing reactions that could be performed, and only achieved a statistical representation of genomic binding, rather than complete saturation coverage. Improvements included concatenations of single "tags" (chIP-SAGE), or Paired-End-diTags of chIP DNA fragments (chIP-PET) (Kim, J. et al., Nat. Methods. 2(1): 47-53, 2005; Chen, J., and Sadowski, I., Proc. Natl. Acad. Sci. USA. 102: 4813-4818, 2005; Bhinge, A. A., et al., Genome Res. 17: 910-916, 2007).

The most significant break-through in ChIP-seq technology came with the development of massively parallel DNA sequencing. The Roche/454 genome sequencer was the first, achieving 300,000 sequencing reads in a single run. Next came Illumina/Solexa, which produced up to 80 million short sequencing reads or tags per run, and Applied Biosystems SOLiD, having a similar short-read capability. The short 25-35 by reads were ideal because 25-35 by of sequence is sufficient to uniquely identify the vast majority of genomic sites. Long sequencing reads only increase cost and provide diminishing marginal returns. Typically 10 million tags are considered to be sufficient.

As powerful as ChIP-seq is, there are technical limitations that preclude its full potential from being realized. A major limitation of ChIP technology is the fragment size and heterogeneity achieved after sonication. Proteins are mapped to their bound DNA fragments, and so the larger and more heterogeneous in size the DNA fragment the larger and more disperse the region that is assigned to the bound protein, making interpolation of the binding location more imprecise. Thus, one may be able to locate a protein only to within ±300 by of its actual bound site, whereas ±1 by is ideal.

A second limitation of ChIP is noise. Noise arises from DNA in the input sample that nonspecifically adheres to the immunoprecipitating resin, and then leaches off during the elution step. Since only a small fraction of a genomic locus is actually crosslinked to the target protein, and since most genomic loci are not bound by the factor, even a small amount of contaminating nonspecific genomic DNA represent a large amount of background. In ChIP-chip experiments, this background decreases the dynamic range of the binding assay, and results in false positives and negatives. The higher resolution inherent in ChIP-seq alleviates this somewhat, but such issues remain. In particular, noise in ChIP-seq requires more sequencing tags to be obtained, which affects costs.

SUMMARY

The ChIP-exo procedure described herein provides a genome-wide ultra-high resolution transcription factor mapping methodology. This methodology will greatly improve the accuracy and robustness of transcription factor mapping, which is expected to substantially advance our understanding of how genes related to human diseases are regulated and mis-regulated. The methods and kits described herein provide a solution to the problems associated with conventional methods (e.g., distribution of tags is dispersed, making interpolation of the binding location more imprecise in ChIP-seq) by moving one end (or the other end) of the fragmented DNA to within a few by of the protein crosslinked to DNA, and significantly diminishing nonspecific contributions (in ChIP-chip and ChIP-seq experiments, >99.9% of the total resulting signal represents genomic DNA that does not reside at the bound site, which decreases the dynamic range and resolution of the binding assay, and results in false positives and negatives).

Accordingly, described herein is a method of identifying a plurality of locations in a genome at which a protein of interest binds to the genome. The method includes the steps of: subjecting a plurality of cells or extract thereof to chromatin immunoprecipitation resulting in at least one nucleic acid fragment bound to the protein of interest; subjecting the at least one nucleic acid fragment bound to the protein of interest to exonuclease treatment resulting in a single-stranded nucleic acid fragment bound to the protein of interest having an exonuclease-treated end demarcating at least one location in the genome at which the protein of interest binds, wherein the exonuclease treatment includes a double-stranded nucleic acid-specific exonuclease that degrades a nucleic acid either in a 5'-to-3' or a 3'-to-5' direction and a single-stranded nucleic acid-specific exonuclease that degrades a nucleic acid in the same direction as the double-stranded nucleic acid-specific exonuclease; and identifying the exonuclease-treated end of the single-stranded nucleic acid fragment bound to the protein of interest. In the method, identifying the exonuclease-treated end of the single-stranded nucleic acid fragment bound to the protein of interest identifies the plurality of locations in the genome at which the protein of interest binds. The protein of interest is any protein that binds directly or indirectly to a nucleic acid, whereas "indirectly" means that binding occurs through interactions with at least one other protein that directly or indirectly binds to the nucleic acid. The step of identifying the exonuclease-treated end typically includes at least one selected from the group consisting of: DNA sequencing, microarrays, and polymerase chain reaction (PCR). In the method, the genome can be any nucleic acid (e.g., a human genome). The single-stranded nucleic acid-specific exonuclease and the double-stranded nucleic acid-specific exonuclease degrade only one nucleic acid strand in either a 5'-to-3' direction or a 3'-to-5' direction. In one embodiment, each of the plurality of locations in the genome at which the at least one protein of interest binds is identified within a five base pair or less limit of resolution. Typically, the plurality of locations constitutes the majority of locations at which the protein of interest binds to the genome.

Also described herein is a method for identifying the nucleotides of a nucleic acid sequence to which a peptide or a polypeptide binds. The method includes the steps of: obtaining a sample including at least a first nucleic acid sequence and at least a first peptide or polypeptide; binding the at least first nucleic acid sequence to the at least first peptide or polypeptide; subjecting the at least first nucleic acid sequence bound to the at least first peptide or polypeptide to exonuclease treatment whereby nucleotides of the at least first nucleic acid that are not bound to the at least first peptide or polypeptide are degraded, resulting in a single-stranded fragment of the at least first nucleic acid, the fragment consisting of nucleotides of the at least first nucleic acid that bind to the at least first peptide or polypeptide, wherein the exonuclease treatment includes a double-stranded nucleic acid-specific exonuclease that degrades a nucleic acid in a 5'-to-3' or a 3'-to-5' direction and a single-stranded nucleic acid-specific exonuclease that degrades a nucleic acid in the same direction as the double-stranded nucleic acid-specific exonuclease; and identifying the nucleotides of the at least first nucleic acid that bind to the at least first peptide or polypeptide. In the method, the step of identifying the nucleotides of the at least first nucleic acid that bind to the at least first peptide or polypeptide can include at least one of: DNA sequencing, microarrays, and polymerase chain reaction (PCR). In one embodiment, the nucleic acid sequence is a human genome. The double-stranded nucleic acid-specific exonuclease can be, for example, lambda exonuclease. The at least one location in the genome at which the protein of interest binds is typically identified with a resolution of five base pairs or less (e.g., 1, 2, 3, 4, 5).

In another embodiment, a kit for identifying at least one location in a genome at which a protein of interest binds is described herein. The kit includes an exonuclease having 5'-3' single-stranded-specific exonuclease activity; an exonuclease having 5'-3' double-stranded-specific exonuclease activity; at least one buffer; at least one wash solution; and instructions for use. The kit can further include at least one elution solution; at least one primer; at least one adapter a least one DNA polymerase a polynucleotide kinase; and a DNA ligase. The exonuclease having 5'-3' double-stranded-DNA-specific exonuclease activity can be, for example, lambda exonuclease, and the exonuclease having 5'-3' single-stranded-DNA-specific exonuclease activity can be, for example, $RecJ_f$ exonuclease.

Also described herein is a kit for identifying at least one location in a genome at which a protein of interest binds. The kit includes an exonuclease having 3'-5' single-stranded-specific exonuclease activity; an exonuclease having 3'-5' double-stranded-specific exonuclease activity; at least one buffer; at least one wash solution; and instructions for use. The kit can further include at least one elution solution; at least one primer; at least one adapter, a DNA polymerase, a polynucleotide kinase; and a DNA ligase.

Further described herein is a method for identifying at least one location at which a protein or peptide of interest binds to a sequence of nucleic acid. In the method, cells, an extract thereof or a sample of protein-nucleic acid complexes are subjected to cross-linking, resulting in cross-linked nucleic acids and proteins. The cells, an extract thereof or a sample of protein-nucleic acid complexes are disrupted to release the cross-linked nucleic acids and proteins. The cells, an extract thereof or a sample of protein-nucleic acid complexes are sonicated resulting in nucleic acid fragments that have at least one protein or peptide of interest cross-linked thereto. The peptide or protein of interest that is cross-linked to at least one nucleic acid fragment is immobilized. The at least one nucleic acid fragment cross-linked to the protein of interest is subjected to exonuclease treatment resulting in a single-stranded nucleic acid fragment of the at least one nucleic acid cross-linked to the protein of interest having an exonuclease-treated end demarcating the at least one location in the genome at which the protein of interest binds, wherein the exonuclease treatment includes a double-stranded nucleic acid-specific exonuclease that degrades a nucleic acid in a 5'-to-3' or a 3'-to-5' direction and a single-stranded nucleic acid-specific exonuclease that degrades a nucleic acid in the same direction double-stranded nucleic acid-specific exonuclease and that hydrolyzes nucleic acid fragments that are not bound to a protein or peptide. The cross-linking is reversed, resulting in single-stranded nucleic acid fragments including the at least one nucleic acid. The single-stranded nucleic acid fragments are subjected to a primer extension reaction resulting in double-stranded nucleic acids comprising the at least one nucleic acid. The exonuclease-treated end of the double-stranded nucleic acids is identified, wherein the exonuclease-treated end is the boundary of the location at which the protein or peptide of interest binds. The location of the nucleotide sequence to which the protein of interest binds can be determined within one base pair (nucleotide). In some embodiments, a protein or peptide of interest binds to multiple locations within a nucleotide sequence (e.g., genome). This method can be used to determine each binding site location for a peptide or protein of interest.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a mammalian (e.g., human) subject to be treated and/or to obtain a biological sample from.

By the terms "transcription factor" and "TF" is meant a protein that binds to the genome, and regulates gene expression.

As used herein, "DNA-protein crosslink" is used to mean covalent bonding of a protein to a nucleic acid, often promoted by use of a chemical crosslinking reagent.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a probe or antibody, is intended to encompass direct labeling of the probe or antibody by coupling (i.e., physically linking) a detectable substance to the probe or antibody.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. Microarrays can be prepared and used by a number of methods, including those described in U.S. Pat. No. 5,837,832 (Chee et al.), PCT application WO95/11995 (Chee et al.), Lockhart, D. J. et al. (Nat. Biotech. 14:1675-1680, 1996) and Schena, M. et al. (Proc. Natl. Acad. Sci. 93:10614-10619, 1996), all of which are incorporated herein in their entirety by reference. In other embodiments, such arrays can be produced by the methods described by Brown et al., U.S. Pat. No. 5,807,522.

As used herein, the phrase "double-stranded nucleic acid-specific exonuclease" means any enzyme that hydrolyzes any part of one strand of a double-stranded nucleic acid in only one direction along the hydrolyzed strand, with that direction being either 5'-to-3' or 3'-to-5', depending upon the classification of the enzyme activity.

By the phrase "single-stranded nucleic acid-specific exonuclease" is meant any enzyme that hydrolyzes any part of a single-stranded nucleic acid in only one direction along the hydrolyzed strand, with that direction being either 5'-to-3' or 3'-to-5', depending upon the classification of the enzyme activity.

As used herein, the phrase "with a resolution of 5 by or less" means that the mapped genomic binding location is within 5 by of its actual location for at least one binding location (e.g., the majority of bound locations) for at least one protein of interest. Similarly, the phrase "with a resolution of 1 by or less" means that the mapped genomic binding location is within 1 by of its actual location for at least one binding location (e.g., the majority of bound locations) for at least one protein of interest.

Although kits and methods similar or equivalent to those described herein can be used in the practice or testing of the present invention, suitable kits and methods are described below. All publications, patent applications, and patents mentioned herein are incorporated by reference in their entirety. In the case of conflict, the present specification, including definitions, will control. The particular embodiments discussed below are illustrative only and not intended to be limiting.

Figure 1:
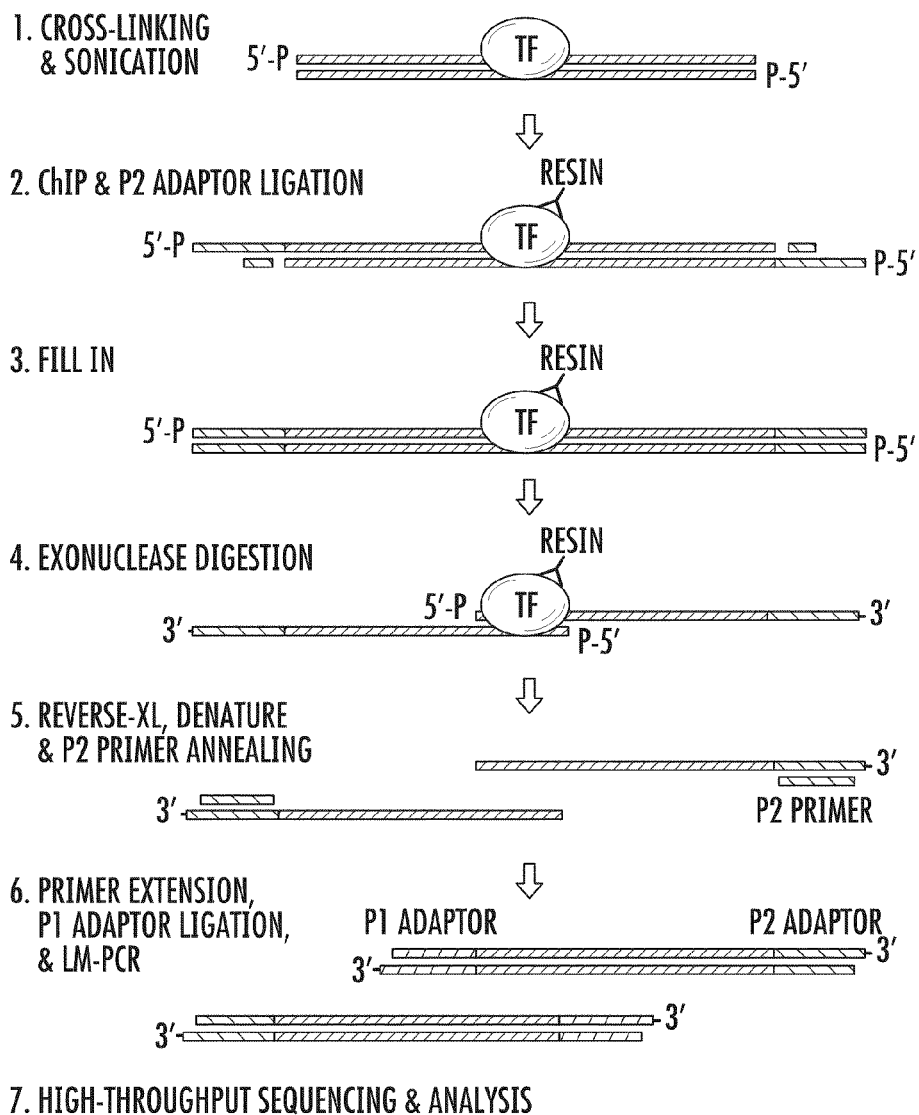
FIG. 1 is a schematic illustration of the strategy for ChIP-exo.

FIG. 3 is a series of plots and graphs showing ChIP-exo products detected by deep sequencing. (A): Distribution of unfiltered, un-normalized Reb1 ChIP-chip, ChIP-seq, and ChIP-exo signals across a 10 kb region of chromosome II. For ChIP-chip (upper panel) individual probe hybridization signals are plotted. Gaps reflect the absence of probes. For ChIP-seq (middle panel) and ChIP-exo (lower panel) each vertical bar corresponds to the number of sequencing reads located at that coordinate. For ChIP-seq and ChIP-exo, respectively, 47 and 14 by were added to all W tag 5'-end coordinates (reflecting the midpoint of the bound location). These values were subtracted from all C strand coordinates. The data were then plotted to be indistinguishable from their source strand. (Distinguishable data of W and C tag 5'-end coordinate were shown on FIG. 6). Insets show a 200 by enlarged view of selected peaks. The red arrows indicate the location of Reb1 recognition sites (TTACCCG) in the inset. (B): Signal intensities from unfiltered, un-normalized ChIP-chip data (Affymetirx, 5 by probe spacing) (23), 2,938,677 unfiltered ChIP-seq sequencing tags, and 2,920,571 unfiltered ChIP-exo sequencing tags (Table 4) were plotted relative to their distance from the Reb1 TTACCCG recognition motif sites (left panel) or a scrambled site (CCGATTC) sites.

FIG. 4 is a series of graphs and plots and a Venn diagram showing results from an evaluation of parameters used to define the complete set of Reb1-bound locations. (A): Diagram demarcating the 5 criteria used to evaluate and identify Reb1 binding locations. Vertical bars under each curve represent the distribution of tags (corresponding to the genomic coordinate of the 5' end of the mapped tag) on the W strand and C strand. Its peak location corresponds to the consensus W and C borders of Reb1 as described on FIG. 2A. The peak-to-peak distance (C-W) defines criterion 1. Criterion 2 reflects the number of replicates that meet criterion 1 at a given location. Criterion 3 reflects the motif DNA sequence that is present. Criterion 4 examines the distance of that motif from the Reb1-bound location. Criterion 5 reflects the tag counts present under each peak. (B-F): A frequency distribution of each criterion for putative bound locations meeting a specified four of the five stringent criteria whose limits are defined in Table 5. (G): Summary of met criteria. The inner pentagon indicates the number of Reb1-bound locations meeting all five stringent criteria. Outer "blades" on the pentagon indicate the number of bound locations missing one (as indicated) of the five stringent criteria defined in Table 5 (but meeting the relaxed criteria). Also indicated is the number of false positives (defined as the average number meeting the indicated criteria for a set of scrambled motifs). (H): Plot of true and false discovery rates versus number of criteria implemented. The x-axis represents the number stringent criteria met (while meeting all 5 at their relaxed limit). The y-axis represents the number of Reb1-bound locations. False positive determination uses scrambled motifs in place of true motifs. (I): Venn diagram of the overlap of genes having Reb1-binding sites from existing ChIP-chip data (P-value threshold of 0.05, (22)) or Reb1-binding sites from ChIP-exo data (meeting at least 5 relaxed criteria). The overlap of genes from ChIP-chip data with other P-value threshold (0.001, 0.01, and 0.1) is shown in FIG. 12.

FIG. 5 is a series of plots showing (A): Composite distribution of 498 Reb1-occupied locations with TTACCCG motif and 247 Reb1-unoccupied TTACCCG motif sites relative to the TSS. The nucleosome distribution is shown for the set of bound genes. Reb1-occupied sites that were upstream of the main peak were associated with upstream divergently transcribed genes. (B): Composite distribution of 466 Reb1-bound locations with a degenerate version (1 mismatch on $1^{st}$, $2^{nd}$, or $7^{th}$ base) of the TTACCCG motif and 5,681 Reb1-unbound version relative to the TSS. Nucleosome distribution for the bound set of genes is also shown. (C): Composite distribution of 690 Reb1-bound secondary locations relative to the TSS. The distribution of Reb1-bound primary locations is shown in the background and by the dashed line. (D): Distance between primary and secondary Reb1-binding sites. 647 of 690 secondary Reb1-bound locations are within 100 by of a primary site.

Figure 6:
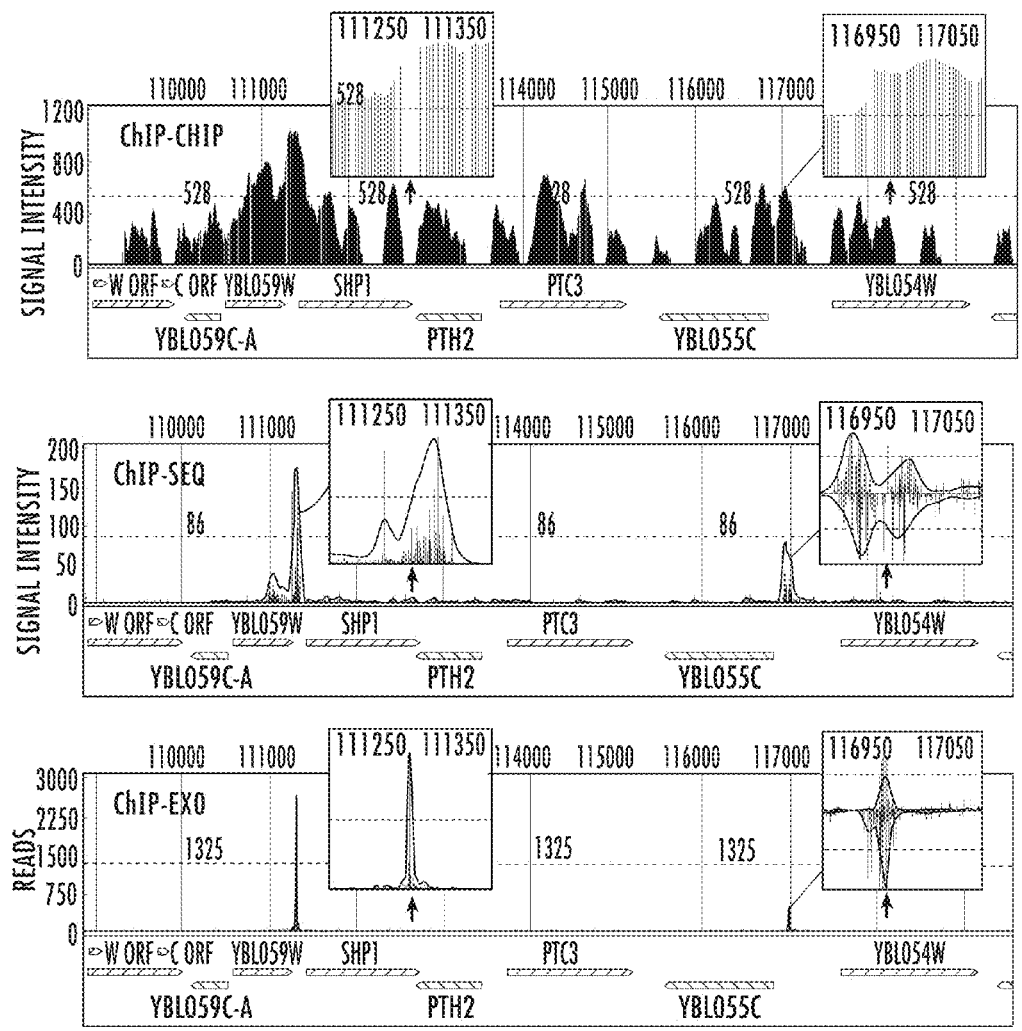

FIG. 6 is a series of plots showing distribution of unfiltered, un-normalized Reb1 ChIP-chip, ChIP-seq, and ChIP-exo signals across a 10 kb region of chromosome II. For ChIP-chip (upper panel) individual probe hybridization signals are plotted. Gaps reflect the absence of probes. For ChIP-seq (middle panel) and ChIP-exo (lower panel) each vertical bar corresponds to the number of sequencing reads located at that coordinate. For ChIP-exo, all tag coordinates (corresponding to the 5' end of the mapped tag) located on the W strand were shifted 14 by downstream, and all tags located on the C strand were shifted 14 upstream, and plotted to be indistinguishable from their source strand. For ChIP-seq, all tag coordinates were shifted in the same way but by 47 bp. Insets show a 200 by enlarged view of selected peaks. Left inset shows a composite of W and C peaks and the right inset shows individual W peak (blue) and C peak (red). The red vertical arrows indicate the location of Reb1 recognition sites (TTACCCG) in the inset.

Figure 7:
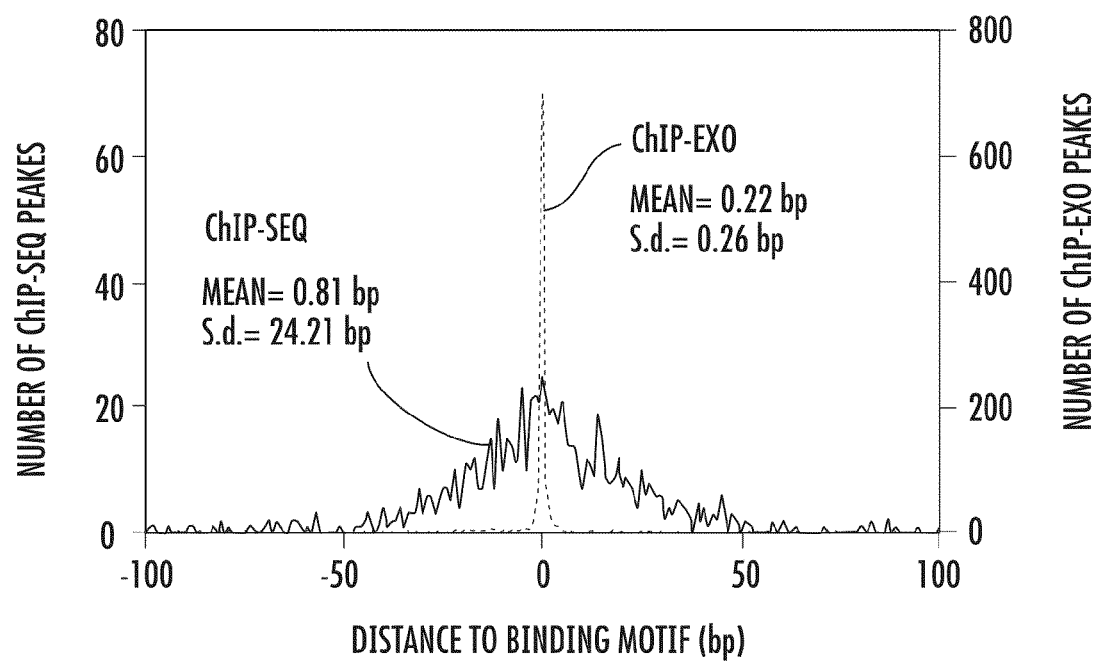

FIG. 7 is a plot showing a comparison of Reb1-bound locations determined by ChIP-seq (866 peaks) and by ChIP-exo (1082 peaks) in relation to the nearest cognate motif (allowing for 1 mismatch in the $1^{st}$, $2^{nd}$, $7^{th}$ base of TTACCCG).

FIG. 8 is a series of Venn diagrams and graphs showing the relationship of ChIP-exo determined locations with other published locations. (A): Venn diagram of the overlap of genes identified as being Reb1-bound from published ChIP-chip data (P-value threshold of 0.05, Harbison, et al. 2004) or from this study (meeting five relaxed criteria). The overlap of genes from ChIP-chip data with using various Harbison et al. P-value thresholds (0.001, 0.01, and 0.1) is shown in the right panel. (B): A similar analysis as in panel A except that the ChIP-seq data generated in this study is examine for false discovery rates. In this case the top 1200 peaks in terms of read counts in each dataset were examined.

FIG. 9 is a pair of graphs showing median read counts. (A): Median read count for TTACCCG and TTACCCT (at non-telomeric, non-tRNA, non-rDNA, and non-ARS regions) compared to TTACCCT at telomeric regions. Reb1-bound TTACCCT at telomeric regions showed greater oocupancy than at non-telomeric regions. (B): Median read count for each Reb1-bound motif. at non-telomeric, non-tRNA, non-rDNA, and non-ARS regions. More degenerate motifs showed less read counts.

FIG. 10 is a table of proteins to which ChIP-exo has thus far been applied.

FIG. 11 is a series of browser shots showing anecdotal examples of ChIP-exo applied to specific proteins. Shown are bound locations in the indicated genome.

FIG. 12 a series of browser shots showing anecdotal examples of ChIP-exo applied to specific proteins. Shown are bound locations in the indicated genome.

Figure 13:
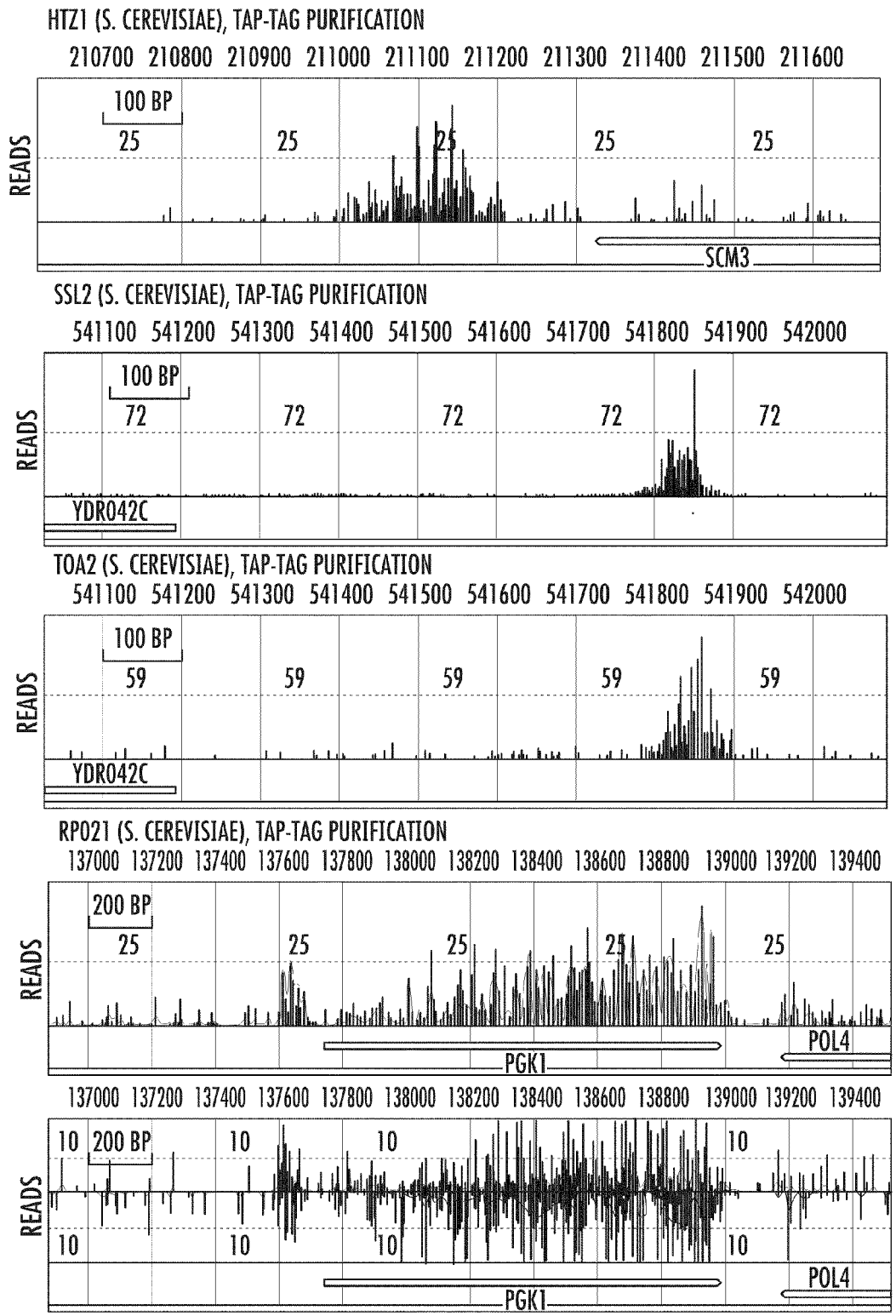

FIG. 13 is a series of browser shots showing anecdotal examples of ChIP-exo applied to specific proteins. Shown are bound locations in the indicated genome.

Figure 14A:
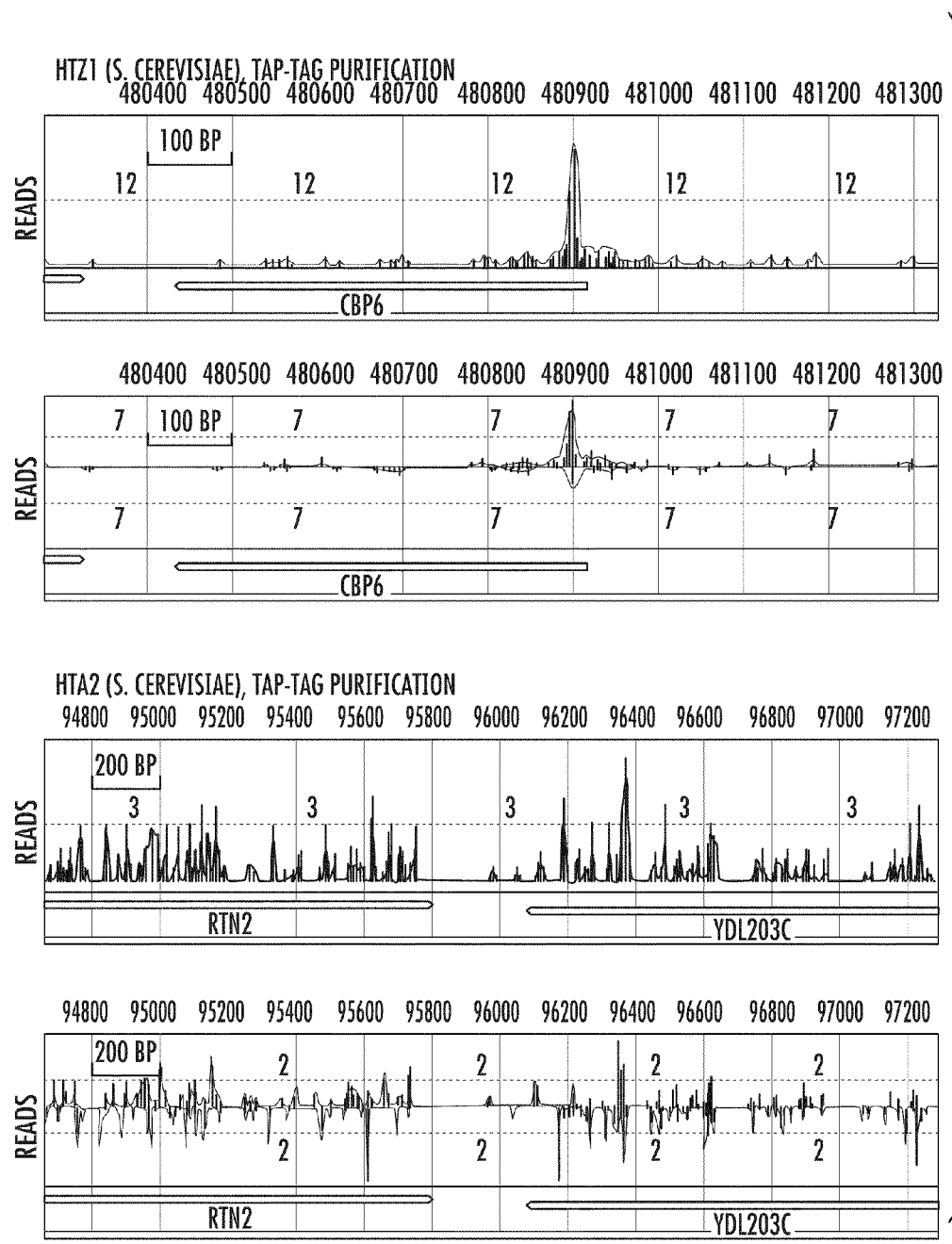
Figure 14B:
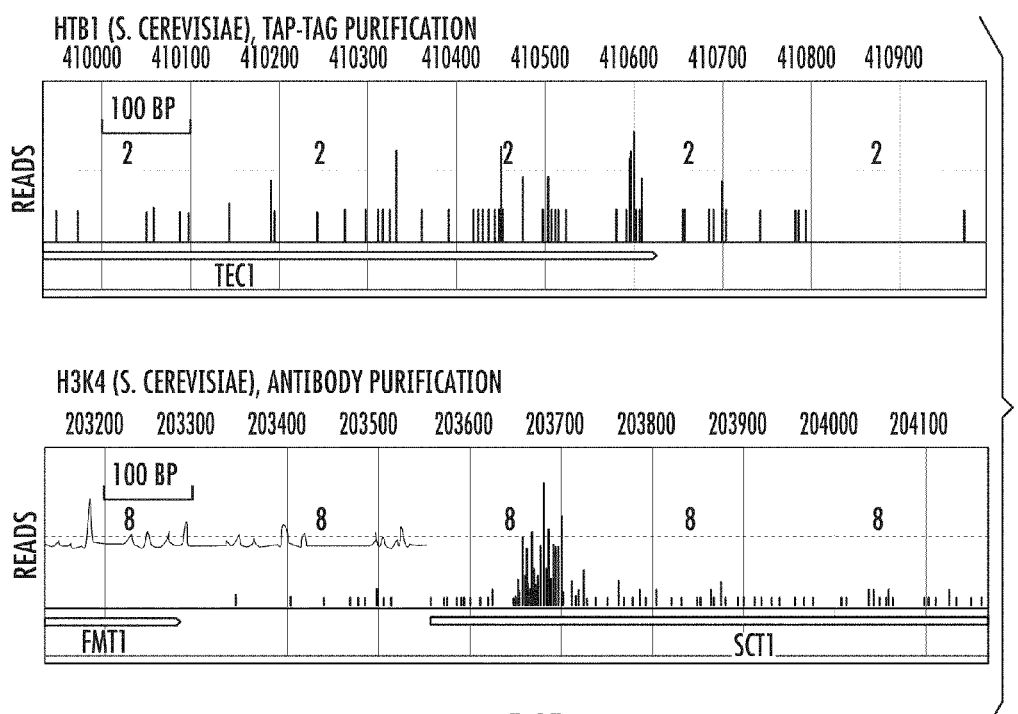

FIG. 14A and FIG. 14B are a series of browser shots showing anecdotal examples of ChIP-exo applied to specific proteins. Shown are bound locations in the indicated genome.

FIG. 15 is a series of browser shots showing anecdotal examples of ChIP-exo applied to specific proteins. Shown are bound locations in the indicated genome.

Figure 16A:
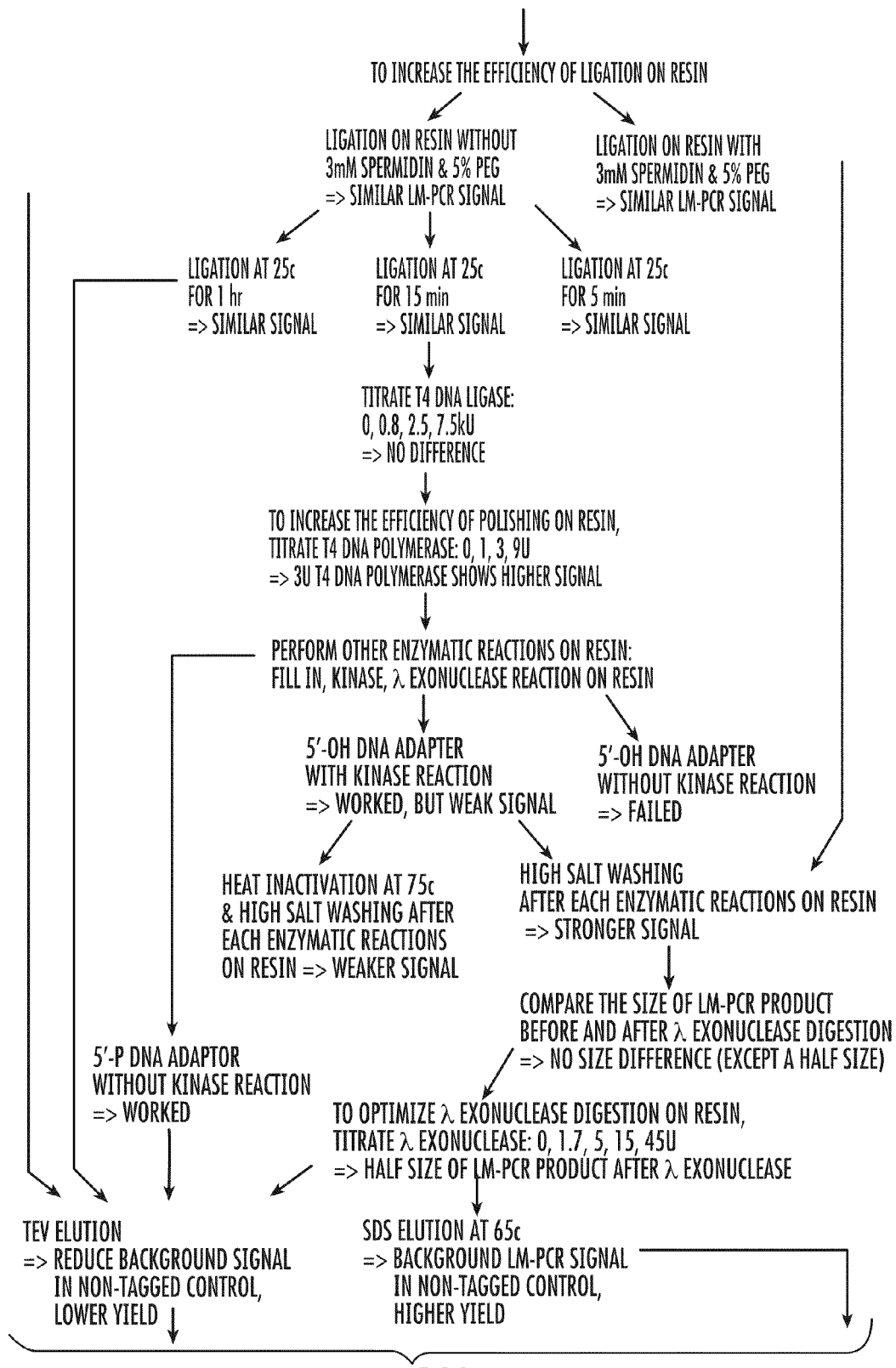
Figure 16B:
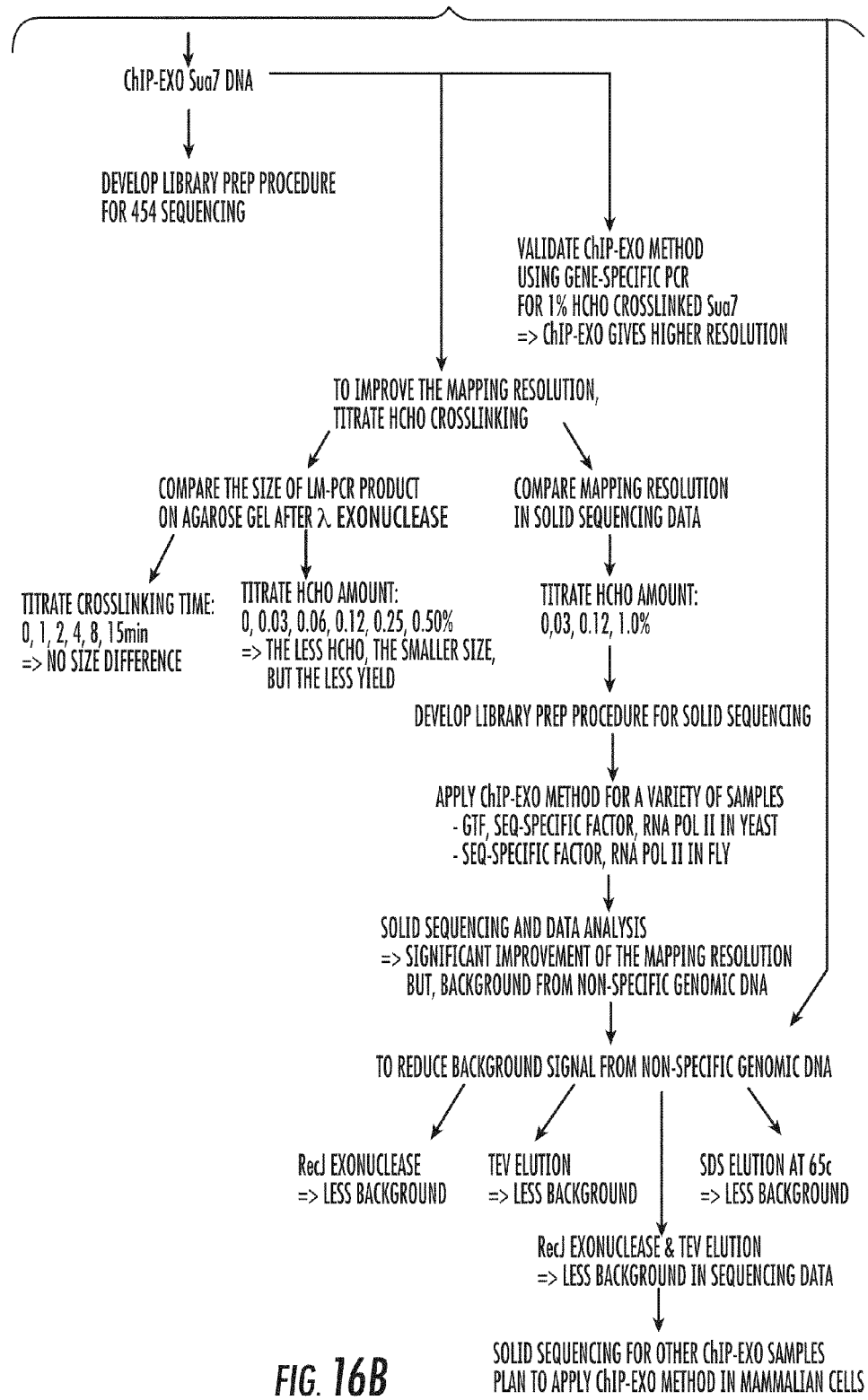

FIG. 16A and FIG. 16B are a flowchart outlining the decision-making process that lead to the development of the methods and kits described herein.

DETAILED DESCRIPTION

Described herein are methods and kits for detecting protein-nucleic acid interactions, in particular, detecting the genomic location to near-base pair resolution at which a particular protein (e.g., transcription factor) binds. A significant improvement of the resolution and dynamic range of the ChIP assay will increase one's ability to determine with confidence where a particular protein is binding in the genome. Importantly, proteins that inefficiently crosslink to DNA (e.g. <5% of their maximal potential occupancy levels or due to indirect crosslinking via another protein) and thus are very difficult to detect, are expected to be detected as significant by the kits and methods described herein. Inasmuch as most aspects of infectious diseases, inborn diseases, and cancers are rooted in the mis-expression of genes, having a better measure of the binding of proteins to genes or promoter regions will enhance the ability of investigators to understand the driving molecular mechanisms behind these human maladies.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). ChIP methods are known in the art and are described in Pugh and Gilmour, Genome Biology vol. 2(4):reviews 1013.1-1013.3, 2001; Lee et al., Nature Protocols vol. 1(2):729-748, 2006; and Collas and Dahl, Front Biosci. Vol. 13:929-943, 2008, as well as in methodology treatises such as Chromatin Immunoprecipitation Assays: Methods and Protocols (Methods in Molecular Biology) by Philippe Collas, 1$^{st}$ edition, 2009, Humana Press, Totowa, N.J.; and DNA-Protein Interactions (Methods in Molecular Biology) by Tom Moss (ed.) and Benoit Leblanc (ed.), 3$^{rd}$ edition, 2009, Humana Press, Totowa, N.J. Ligation-mediated polymerase chain reaction (LM-PCR) methods are also known in the art and are described, for example, in Ngoc et al., FEMS Microbiol. Lett. Vol. 288:33-39, 2008; and Tagoh et al., Methods Mol. Biol. Vol. 325:285-314, 2006.

ChIP-Exo

Described herein are methods, systems and kits for identifying the location at which a protein binds in any prokaryotic or eukaryotic genome. The methods, systems and kits provide for determination of a genomic location to near base-pair resolution (the median resolution is less than 5 by (e.g., 1, 2, 3, 4, 5 bp) for tested sequence-specific DNA binding proteins that occupy their cognate sites at least 5% of the time). A typical method for identifying the location at which a protein binds in a genome includes several steps that are performed in a conventional ChIP assay, but further includes use of an exonuclease to hydrolyze the nucleic acid on one strand in the 5'-to-3' direction until it reaches the protein crosslinked to the nucleic acid. In some embodiments, however, an exonuclease that hydrolyzes a nucleic acid in a 3'-to-5' direction can be used. DNA sequences downstream of the block and on the same nucleic acid strand remain intact, and are used to identify the nucleic acid molecule, including the exonuclease blockage point. A typical method includes the steps of obtaining a sample from an organism; performing a chromatin immunoprecipitation assay on the sample using one or more antibodies that specifically bind to the protein; contacting the sample with the exonuclease prior to crosslink reversal under conditions in which the exonuclease digests a nucleic acid strand having the protein crosslinked thereto only on one side or the other of the protein (FIG. 1), whereby regions of nucleic acid downstream of the crosslinking point are resistant to exonuclease hydrolysis and thus isolated; and identifying the genomic location of the regions of nucleic acid to near by resolution. These steps, as well as the conventional ChIP steps used in methods, kits and systems described herein, are described in more detail below.

Any type of cell or reconstituted protein-nucleic acid complex can be used in ChIP, and thus ChIP-exo is applicable to both DNA and RNA, and to complexes of nucleic acids assembled in vitro. The procedure is also applicable in the absence of crosslinking, as long as the protein remains bound to the nucleic acid. A population of cells (or in vitro assembled complexes) is incubated with a chemical crosslinking reagent such as formaldehyde, which crosslinks proteins to each other and to nucleic acids such as DNA and RNA. Any suitable crosslinking reagent can be used The purpose of the crosslinker is to preserve in vivo protein-nucleic acid interactions during the stringent work-up conditions that are meant to diminish nonspecific contamination. The crosslinking reaction is almost instantaneous, and provides a snapshot of the protein-nucleic acid interactions taking place in the cell. The next step of the assay requires cell disruption and washing of the insoluble chromatin to remove non-chromatin soluble proteins. The chromatin is then fragmented and solubilized using sonication. Sonication randomly shears DNA to a size range of about 300 by in yeast and 0.5-1 kb in vertebrates, although more intense sonication can create smaller fragment sizes.

The next common step in ChIP is to purify a chromatin/nucleic acid binding protein, typically in the form of immunoprecipitation where an immobilized antibody against the protein is used to selectively pull out of solution the target protein. Along with the immunopurified protein comes any nucleic acid to which it is crosslinked. Buffer and wash conditions are of sufficient stringency (usually with low levels of the detergent SDS) that retention of nucleic acid contaminants that have not been directly or indirectly crosslinked to the target protein are diminished but not eliminated.

In the standard ChIP assay, the bound crosslinked DNA is detected by PCR (after reversing the crosslink). This requires the experimenter to know, within a few hundred bp, where the protein is bound in the genome, in that specific primers need to be designed to the interrogated region. This is in contrast to the methods, systems and kits described herein (collectively referred to herein as "ChIP-exo"), however, in which the DNA sequences on one side of the crosslinked site are removed from each strand (FIG. 1). By removing this DNA, the uncertainty of where the crosslinked protein resides is reduced from several hundreds of by to a few bp. Removal of flanking DNA can be accomplished with nucleases, but only exonucleases can be made to operate directionally. Instead of a nuclease that hydrolyzes all flanking DNA, a nuclease is chosen that digests only one strand on both sides. Use of a nuclease (e.g., lambda exonuclease) that digests only one strand on both sides overcomes the problem of general nucleases (endonucleases or double-stranded exonucleases) that leave so little DNA that it cannot be uniquely identified in the genome. Approximately 25 by is needed for unique identification of most DNA sequences in a genome. The same ChIP-exo strategy is applicable to RNA, where a strand-specific RNA exonuclease is employed, although some prior fragmentation or decapping of the RNA may be required.

Lambda exonuclease (as one example of a potential strand-specific exonuclease) catalyzes the 5'-to-3' removal of 5' mononucleotides from duplex DNA, leaving the complementary sequence intact. In principle, the exonuclease might stop when it finds a protein crosslinked to the nucleic acid, due to physical blockage. The notion of blockage is conjecture unless demonstrated otherwise, in that the active site of the exonuclease might accommodate a nucleic acid adduct such as a crosslinked amino acid. The invention therefore requires the exonuclease to remove flanking 5' nucleic acid up to the site of blockage caused by the crosslinked protein. For ChIP-exo applied to DNA, if the ends of the ChIP DNA are "marked" with a known DNA sequence such as a DNA adaptor prior to exonuclease digestion (green in FIG. 3), then later sequencing of the DNA fragment will allow the end at the crosslinked barrier to be distinguished from the other end generated during fragmentation by sonication.

The next step is to reverse the crosslink, separate the strands, synthesize complementary DNA, then ligate the final adapter to create a sequencing library. ChIP-exo is optimally performed in conjunction with single-molecule DNA sequencing (either true single molecule or clusters of identical clones) to identify individual DNA molecules, which can be accommodated by Illumina, Applied Biosystems, Roche, and other deep sequencing technologies. Hybridization-based detection platforms could also be used but provide less resolution.

A variation of the ChIP-exo procedure described above achieves digestion of only one side or the other by randomly blocking one end or the other of the DNA (e.g. attachment of a large molecule such as biotin, or the removal of a phosphate, may create blocks). Any suitable exonuclease can be used, for example, double-strand exonucleases such as Bal31 might be used, or a combination of 5'-3' and 3'-5' single-stranded exonucleases might be used in this procedural variation.

Within the inventive methods, kits and systems described herein, several advantageous outcomes are achieved with ChIP-exo. First, the nuclease hydrolyzes nucleic acid up to within a few by of the protein binding site, thus defining the location of the bound protein. Second, the other flank is undigested and thus provides sufficient length in most cases to uniquely identify the genomic location of the crosslinked protein by DNA sequencing. Third, since the crosslink blocks the nuclease, non-crosslinked contaminating nucleic acid will be hydrolyzed, and rendered unclonable, thereby reducing noise from background. Importantly, the exonucleases described above would not work unless one side is blocked, otherwise it will chew in from both flanking DNA ends, leaving too little DNA to uniquely identify.

The overall procedure for this method, which is referred to as ChIP-exo, is depicted in FIG. 1. Referring to step 1 in FIG. 1, yeast cells are crosslinked with formaldehyde and lysed with glass beads. Cells may be lysed by any physical or chemical means. The crosslinked chromatin is sonicated and broken down to 100-400 by chromatin fragments, although other sizes will work. Referring to step 2 in FIG. 1, the transcription factor of interest is immunoprecipitated. An untagged strain (BY4741) serves as a negative control for the immunoprecipitation. The sample then remains on the resin. Resin-bound sonicated ChIP DNA is polished by T4 DNA polymerase (or equivalent) and ligated with P2 adaptors (green) using T4 DNA ligase. The P2 adaptor may be any DNA sequence that is compatible with genomic sequencing. Use of these enzymes is standard for this type of reaction. Referring to step 3 in FIG. 1, the nick between the 3' end of the template DNA and the 5' end of the P2 adaptor is filled in by phi29 DNA polymerase (or equivalent), which is within the specifications of this enzyme. Referring to step 4 in FIG. 1, lambda exonuclease (or equivalent) is used to digest one DNA strand in the 5' to 3' direction and is expected to stop when it encounters the bound protein (as demonstrated below). Thus, both borders of the DNA occupied by the bound protein are identified. Uncrosslinked nonspecific DNA may also contaminate the resin. Lambda exonuclease will only hydrolyze half this contaminating DNA because it is required to act on double-stranded DNA. Thus, single-stranded DNA is a product of lambda exonuclease. To remove this, a 5'-to-3' single-stranded exonuclease (e.g. recJ$_f$) is included in the reaction. Note that the crosslinked DNA is resistant to this exonuclease, and thus this enzyme is intended to remove contaminating uncrosslinked single-stranded DNA. Referring to step 5 in FIG. 1, after lambda exonuclease digestion, the protein-DNA complex is eluted from the resin, by reversing the crosslinks (1 hr incubation at 65° C.). Other elution procedures may be employed, but must follow a method that reverses the crosslinks.

The resulting eluted single-stranded DNA is annealed with a primer complementary to the ligated adaptor (e.g. P2 primer step 5 in FIG. 1), such that DNA polymerization can proceed across the ChIP DNA. Referring to step 6 in FIG. 1, dsDNA is then synthesized from each single-stranded DNA by P2 (or equivalent) primer extension using phi29 DNA polymerase (or equivalent). Then, this DNA is ligated with a second sequencing adaptor (e.g. P1, as either blunt-ended or sticky-ended using an A overhang) and is amplified by ligation-mediated polymerase chain reaction (LM-PCR), if necessary. The P1 (or equivalent) adaptor may be any DNA sequence that is compatible with genomic sequencing. LM-PCR is optional, and may be needed due to a typically low yield of the DNA. Since different efficiencies of amplification might occur with each fragment (e.g. small fragments amplify better than larger ones), the number of cycles should be kept to a minimum. Regardless, there are statistical methods to detect and correct for such potential PCR biases (e.g. number of unique P2/ChIP-DNA borders). Referring to step 7 in FIG. 1, the resulting DNA sample is used for high-throughput sequencing, using, for example, the Illumina/Solexa GAII or AB SOLiD system. Importantly, the first (or second) sequenced base off of the P1 (or equivalent) primer marks the genomic location of the left or right border of the crosslinked protein (depending upon whether the sequence maps to the "+" or the "−" strand) defined by lambda exonuclease. All remaining sequenced bases are used to uniquely specify the genomic location of the sequence tag.

Separate sequencing of individual DNA molecules that are truncated at either the right or left border of the protein-DNA crosslink is used to identify the right and left borders (i.e. left border on "+" vs. right border on "−" strand) of the bound protein. The "footprint" size is determined by the number of base pairs between the left and right borders of the bound protein. In addition, the relative amount of protein binding is determined by the normalized number of sequencing reads clustered under the detected peak. GeneTrack is one means for peak detection and to generate a genome-wide browser of the tag distribution (Albert et al., Bioinformatics, 2008). However, the UCSC browser and any other peak detection method should suffice. GeneTrack software was previously developed for such a purpose, and its use has been reported in several publications (Albert et al., Bioinformatics, 2008; Mavrich et al., Genome Res., 18:1073-1083, 2008; Mavrich et al., Nature, 453:358-362, 2008).

Possible pitfalls and solutions have been addressed. For example, one possible pitfall is that the crosslinked protein is not likely to protect enough DNA from a nuclease that it could be uniquely identified (25-35 bp). The solution is to use lambda exonuclease, which leaves intact one strand on each side of the crosslink that can be used for unambiguous genomic identification. Another example of a possible pitfall is that the protein-DNA crosslink may not block the exonuclease. The solution is to determine whether lambda exonuclease destroys all ChIP DNA, or whether it just reduces its size by about half (see FIG. 1 for an illustration). Yet another example of a possible pitfall is whether or not the lambda exonuclease in combination with recJ$_f$ will eliminate nonspecific contaminant DNA. The solution is to test lambda exonuclease on "ChIP" DNA from a negative control (that lacks the antibody epitope). A further example of a possible pitfall is that elution of the ChIP material prior to exonuclease treatment may result in crosslink reversal (heat, SDS, proteases). The solution is to perform the exonuclease digestion on the resin, before elution (see FIG. 1). A final example of a possible pitfall is a potential inability to distinguish the exonuclease-blocked end of the DNA from the distal end generated during sonication. The solution is to ligate a defined adapter sequence onto both ends prior to exonuclease treatment. Exo treatment then removes the adapter off of the exo-blocked end (FIG. 1).

Kits

Described herein are kits for detecting protein-DNA interactions, in particular, detecting the genomic location to near-base pair resolution at which a particular protein (e.g., transcription factor) binds. A typical kit includes an exonuclease that digests one strand of linear duplex DNA in the 5' to 3' direction (e.g., lambda exonuclease), an exonuclease having 5'-3' single-stranded-DNA-specific exonuclease activity (e.g., RecJ exonuclease), at least one buffer, at least one wash solution, and instructions for use. In one embodiment, a kit includes polishing enzymes for creating blunt-ended or A-tailed fragments, two ligatable sequencing adapters, DNA ligase, an exonuclease that digests one strand of linear duplex DNA in the 5' to 3' direction (e.g., lambda exonuclease), an exonuclease having 5'-3' single-stranded-DNA-specific exonuclease activity (e.g., RecJ exonuclease), a primer, an extension enzyme (DNA polymerase), at least one buffer, at least one wash solution, and instructions for use.

EXAMPLES

The present invention is further illustrated by the following specific examples. The examples are provided for illustration only and should not be construed as limiting the scope of the invention in any way.

Example 1

Demonstration of Reduction to Practice

The feasibility of the proposed ChIP improvement plan is largely dependent upon whether lambda exonuclease (or equivalent) will stop when encountering a protein bound or crosslinked to DNA, in which the protein is expected to be at least partially denatured. To validate this aspect of the plan, a study was initiated to determine whether lambda exonuclease will shorten, but not eliminate, ChIP DNA. Several TAP (tandem affinity purification)-tagged transcription factors including Sua7 were tested in yeast (general transcription factor TFIIB), Rap1 (sequence-specific activator/repressor), Reb1 (sequence-specific regulator), Rpo21 (RNA polymerase II), and many others (Gal4, Ume6, Sok2, Phd1, Taf1, Ssl2, Htz1, Hta2, and Toa2), as shown in FIGS. 15-18. All have given the same result, which suggests that the methods described here will be broadly applicable to a wide range of transcription factors in different organisms. GAF (GAGA-binding protein) and Rpb3 (RNA polymerase II) were tested in fly, and p53 (tumor protein 53) and CTCF (CCCTC-binding protein) were tested in human, all leading to the same conclusion of broad applicability (FIG. 15). Sua7 occupancy at RPL3 was determined using gene-specific PCR of λ exo-digested ChIP DNA vs. sonicated ChIP DNA, and serves as proof-of-principle prior to committing to full genomic sequencing.

In this trial experiment, two S. cerevisiae strains were used: Sua7-TAP and BY4741. Sua7-TAP contains a C-terminal TAP tag that is recognized by an IgG antibody. BY4741 is the untagged parent, and serves as a negative control. The solubilized sonicated ChIP input chromatin DNA was sheared to a size range of <500 by for both the test and control samples. After ChIP, and subsequent washing, but before elution or any other treatment, equal amounts of DNA were present in both the Sua7-TAP and BY4741 negative control as detected by LM-PCR. Thus, at this stage most of the immunoprecipitated DNA is nonspecific, as expected. Locus-specific ChIP (e.g. at the active RPL3 promoter) would show a specific enrichment in the Sua7 sample. Importantly, after lambda exonuclease treatment of the ChIP material that still resides on the resin, the DNA in the control BY4741 sample disappears. Importantly, the DNA in the Sua7 sample appears at a smaller size range (approximately half) than the undigested sample. This result demonstrates that 1) lambda exonuclease diminishes background, 2) the protein-DNA crosslink effectively blocks lambda exonuclease, and 3) exonuclease digestion can be successfully performed on an immobilized support (ChIP resin).

Next, validation of ChIP-exo at specific loci was attempted. The ribosomal protein gene RPL3 was chosen because it is highly active and thus expected to be enriched with the general transcription factor Sua7/TFIIB. Gene-specific PCR with primers spaced every 50-100 by throughout the RPL3 promoter region was used to map the upstream border and the downstream border of the ChIP DNA. Primers that span the border will not amplify the ChIP DNA, whereas primers within the border will amplify the ChIP DNA. For this promoter, TFIIB was expected to reside around 120 by upstream of the ORF start site, which is where the TATA box is often found. This expected location was used as a guide in designing the positions of the primers. Lambda exonuclease-digested chIP DNA provided a narrower range of genomic coordinates for Sua7 occupancy compared to ChIP DNA produced by standard methods (no exonuclease).

At this lower level of resolution, standard ChIP placed the left border of the ChIP DNA fragment broadly between −170 and −135, whereas ChIP-exo placed the left border between −135 and −90. On the right border the range was −30 to +45 for standard ChIP and between −165 and −100 for ChIP-exo. Thus, standard chIP placed the TFIIB binding site between −170 and +45 (>200 by range), whereas locus-specific PCR coupled to ChIP-exo placed it between −122 and −110 (<50 by range). Note that the resolution in this test was limited by the placement of the primers.

Next, primers were spaced every 5-15 bp, throughout the narrowed region defined above. The results are summarized in Table 1 for RPL3, and for further validation, a second active ribosomal protein gene RPL5. Both placed the right and left, borders of Sua7 binding to within ~12 by of each other. These results demonstrate that within the limits of a PCR-based assay the ChIP-exo assay can identify DNA binding site midpoint to within a ±~12 by range, which is more than 20 times the resolution afforded by traditional sonication-only based ChIP assays.

TABLE 1

Sua7 binding sites at RPL3 and RPL5 loci using gene-specific PCR of Exo-digested ChIP

| | RPL3 | | | RPL5 | | |
|---|---|---|---|---|---|---|
| | Gene-specific PCR of exo-digested ChIP | | High-density array of | Gene-specific PCR of exo-digested ChIP | | High-density array of |
| | Left border | Right border | sonicated ChIP | Left border | Right border | sonicated ChIP |
| Range | −125 to −119 bp | −121 to −101 bp | — | −107 to −93 bp | −93 to −85 bp | — |
| Midpoint | −122 bp | −110 bp | — | −100 bp | −89 bp | — |
| Binding site | −116 bp | | −118 bp | −95 bp | | −103 bp |

In the next phase of the experimentation, the Sua7/TFIIB ChIP-exo material was sequenced using the Applied Biosystems SOLiD genome sequencer. Approximately 5 million mapped tags were obtained. For comparison, a standard sample (no exo) was subjected to hybridization on Affymetrix 1.0 tiling arrays (5 by probe spacing). The results were processed through GeneTrack software and an example comparison at a specific locus (HOG1 gene) was made. The ChIP-exo procedure produced a tight cluster of tags at the expected position in the HOG1 promoter, whereas standard ChIP-chip produced a broad, but significant occupancy profile. This result suggests that the ChIP-exo procedure holds some potential for increased resolution and decreased background.

Example 2

ChIP-Exo Sequencing Run Summary

TABLE 2

Sequencing Run Summary

| | | | | Run metrics | |
|---|---|---|---|---|---|
| Sample | Purpose of experiment | Read length | Barcode | Total tag count | Uniquely aligned tags |
| ChIP-exo Sua7 (1%) | To show ChIP-exo method using general transcription factor (1% formaldehyde) | 35 bp | P1-ATCNN | 10,538,219 | 5,497,628 |
| ChIP-exo Sua7 (0.12%) | To reduce background signal using less crosslinking (0.12% formaldehyde) | 35 bp | P1-ACCC | 382,875 | 177,506 |
| ChIP-exo Sua7 (0.12%, | To reduce background signal using | 35 bp | P1-GGAG | 710,656 | 202,624 |

TABLE 2-continued

Sequencing Run Summary

| Sample | Purpose of experiment | Read length | Barcode | Total tag count | Uniquely aligned tags |
|---|---|---|---|---|---|
| RecJ) | RecJ exonuclease (0.12% formaldehyde) | | | | |
| ChIP-exo Sua7 (0.12%, TEV) | To reduce background signal using TEV protease elution (0.12% formaldehyde) | 35 bp | P1-AGGT | 1,021,116 | 173,609 |
| ChIP-exo Sua7 (0.12%, RecJ, TEV) | To reduce background signal using RecJ, TEV elution, and more lambda exonuclease (0.12% formaldehyde) | 35 by | P1-GATC | 1,914,119 | 763,253 |
| ChIP-exo Sua7 (large 0.12%, RecJ, TEV) | To improve the mapping resolution using less crosslinking (large vol. of 0.12% formaldehyde) | 35 bp | P2-GGGCTTNNNNN (SEQ ID NO: 1) | 554,383 | 147,884 |
| ChIP-exo Sua7 (large 0.03%, RecJ, TEV) | To improve the mapping resolution using less crosslinking (large vol. of 0.03% formaldehyde) | 35 bp | P2-TAGCGTNNNNN (SEQ ID NO: 16) | 392,016 | 47,141 |
| ChIP-exo Reb1 (1%) | To show ChIP-exo method using seq-specific factor (1% formaldehyde) | 35 bp | P1-GATC | 3,500,412 | 1,099,632 |
| ChIP-exo Reb1 (0.12%, RecJ, TEV) | To improve the mapping resolution using less crosslinking (0.12% formaldehyde) | 35 bp | P1-GGAG | 706,110 | 185,933 |
| ChIP-exo Rpo21 (1%) | To show ChIP-exo method using RNA polymerase II (1% formaldehyde) | 35 bp | P1-AAGNN | 13,001,576 | 5,554,330 |
| ChIP-exo Rpo21 (0.12%, RecJ, TEV) | To improve the mapping resolution using less crosslinking (0.12% formaldehyde) | 35 bp | P1-CGTA | 5,318,340 | 1,973,668 |

TABLE 2-continued

Sequencing Run Summary

| Sample | Purpose of experiment | Read length | Barcode | Run metrics | |
|---|---|---|---|---|---|
| | | | | Total tag count | Uniquely aligned tags |
| ChIP-exo Htz1 (0.12%, RecJ, TEV) | To show ChIP-exo method using histone varient (0.12% formaldehyde) | 35 bp | 2-ACCC | 7,000,000 | 2,258,855 |
| ChIP-exo Htz1 (large 0.12%, RecJ, TEV) | To improve the mapping resolution using less crosslinking (large vol. of 0.12% formaldehyde) | 35 bp | P2-ACGGAGNNNN (SEQ ID NO: 2) | 3,044,839 | 892,738 |
| ChIP-exo Htz1 (large 0.03%, RecJ, TEV) | To improve the mapping resolution using less crosslinking (large vol. of 0.03% formaldehyde) | 35 bp | P2-AGCGTTNNNN (SEQ ID NO: 3) | 492,799 | 99,358 |
| ChIP-exo Hta2 (large 0.12%, RecJ, TEV) | To show ChIP-exo method using histone H2A (0.12% formaldehyde) | 35 bp | P2-GGGCTTNNNN (SEQ ID NO: 1) | 4,332,006 | 1,195,295 |
| ChIP-exo Htb1 (large 0.12%, RecJ, TEV) | To show ChIP-exo method using histone H2B (0.12% formaldehyde) | 35 bp | P2-CGGGTCNNNN (SEQ ID NO: 4) | 3,119,656 | 845,148 |
| ChIP-exo fly GAF (1%) | To show ChIP-exo method using fly seq-specific factor (1% formaldehyde) | 35 bp | P1-CGTA | 2,269,880 | 531,409 |
| ChIP-exo fly Rpb3 (1%) | To show ChIP-exo method using fly RNA polymerase II (1% formaldehyde) | 35 bp | P1-GATC | 13,392,366 | 1,852,343 |
| 18 samples | Optimize for 8 DNA-binding proteins in yeast and fly under a variety of experimental conditions | | | 72 million tags | 24 million tags |

Example 3

Mapping Results

The mapping error of ChIP-Exo and ChIP-chip for Reb1 was determined. The binding locations for Reb1 were experimentally determined by ChIP-exo Reb1 (0.12%, RecJ, TEV) sequencing and ChIP-chip high-density tiling array (Venters, B. J., and Pugh, B. F., Genome Res. 19: 360-371, 2009). A cumulative error plot was constructed and showed the maximum allowable by distance between predicted and measured locations. Only data that were within 100 by of a reference point (Reb1 binding motif) were considered. The plot indicated that for sites occupied >5% of the time, ChIP-exo resulted in 90% of the bound locations having an accuracy of 1 by or less; and for sites occupied <5% of the time (low efficiency binding), 70% of the bound locations had an error of 1 by or less. This contrasts with ChIP-chip in which only ~10% of the bound locations were accurate to within 1 bp. Based upon these results ChIP-exo is up to 100 times more accurate than ChIP-chip.

Table 2 and the experiments described below illustrate specific examples of the increased precision that implementation of the ChIP-exo method provides, compared to conventional methods (ChIP-chip). In the following experiments, ChIP exo provided a much tighter peak compared to the broad peak of ChIP-chip, and thus provided greater resolution. The first series of experiments are summarized in Table 2, and reflect early attempts at optimizing ChIP-exo experimental methods and test its applicability in different species of organisms. FIG. 10 summarizes the ChIP-exo experiments performed on different proteins, after the general ChIP-exo procedure had been optimized. FIG. 11-15 illustrate specific examples of bound locations across the indicated genomes. Such examples are typical of bound locations. Each peak of sequencing tags represents a bound location. As can be seen from FIGS. 14 and 19 as well as the experiments described in these Examples, the methods of the invention were successfully used with several cells from several different organisms. In the experiments described herein, yeast cells (e.g., *S. cerevisiase*), insect cells (*Drosophila melanogaster*), and human cells (e.g., bone cultures and HeLa cells) were used. The methods and kits described herein are applicable to any type of cell from any type of organism.

Example 4

ChIP-Exo Flowchart

Referring to FIG. 16, this flow chart outlines the decision making process that lead to the methods and kits described herein. The purpose of this flow chart is to demonstrate the invention is not obvious and that many pitfalls needed to be worked out.

Example 5

ChIP Exo Protocol for Fly and Mammalian Cells

A ChIP-exo protocol for fly and mammalian cells is nearly the same as a ChIP-exo protocol for yeast cells. However, there are some differences in lysis and elution steps.

Cell Lysis for Fly:
1. Microfuge the crosslinked cells at 3,500 rpm for 5 min at 4° C.
2. Resuspend cell pellet in 1 ml of cold 1× PBS buffer.
3. Microfuge the cells at 3,500 rpm for 5 min at 4° C. Discard supernatant.
4. Add 1 ml of Lysis Buffer per $1 \times 10^8$ cells.
5. Vortex to suspend cells.
6. Incubate the cells on ice for 10 minutes to allow cell lysis.
7. Microfuge lysate at 3,500 rpm for 5 min at 4° C.
8. Transfer lysates into 1.5 ml eppendorf tubes.

Cell Lysis for Human Cells:
1. Microfuge the crosslinked cells at 1,500 rpm for 6 min at 4° C.
2. Resuspend cell pellet in 1 ml of cold 1× PBS buffer.
3. Microfuge the cells at 1,500 rpm for 6 min at 4° C. Discard the supernatant.
4. Repeat 2 and 3.
5. Resuspend cell pellet in 1 ml of cold 1× PBS buffer,
6. Transfer the cell pellet to 15 ml falcon tube.
7. Resuspend the cell pellet with 8 ml of SDS-Lysis buffer per $1 \times 10^8$ cells.
8. Pipette up and down several times.
9. Rotate the cells for 10 minutes at 4° C.
10. Microfuge lysate at 1,500 rpm for 6 min at 4° C. Discard the supernatant.
11. Transfer lysates into 1.5 ml eppendorf tubes.

ChIP buffers for fly and mammalian cells are slightly different from ChIP buffers for yeast cells.

TABLE 3

| | ChIP buffers | | |
| --- | --- | --- | --- |
| | Yeast | Fly | Human |
| Immunoprecipitation | FA Lysis Buffer | IP Buffer | IP Buffer |
| Wash 1 | FA High Salt Wash Buffer | High Salt Wash Buffer | Buffer 500 |
| Wash 2 | FA Wash Buffer 3 | Lithium Wash Buffer | LiCl/Detergent Buffer |
| Elution | ChIP Elution Buffer | Elution Buffer | Bicarbonate/SDS Buffer |

Elution for Fly Cells:
1. Resuspend resin in 250 ul Elution Buffer.
2. Rotate at room temperature for 15 min.
3. Microfuge eluates at 3,500 rpm for 2 min.
4. Transfer eluate to 1.5 ml LoBind tube.
5. Repeat 1 to 4.
6. Combine eluate to 1.5 ml LoBind tube.
7. Add 20 ul of 5M NaCl.
8. Heat at 65° C. for 4 hours (or overnight) to reverse crosslinks.
9. Add 15 ul of 1M Tris-HCl (pH 7.8) and 1.5 ul of 20 mg/ml Proteinase K to eluate.
10. Incubate for at least 30 min at 37° C.

Elution for Human Cells:
1. Resuspend resin in 150 ul Bicarbonate/SDS Buffer.
2. Shake at low speed (speed 3) on a vortexer for 15 min.
3. Microfuge eluates at 3,500 rpm for 2 min.
4. Transfer eluate to 1.5 ml LoBind tube.
5. Repeat 1 to 4.
6. Combine eluate to 1.5 ml LoBind tube.
7. Heat at 65° C. for 4 hours (or overnight) to reverse crosslinks.
8. Add 1.5 ul of 20 mg/ml Proteinase K and 1 ul of 10 mg/ml RNAse A to eluate.
9. Incubate for at least 30 min at 37° C.

Example 6

ChIP-Exo: A Technique to Map a Nearly Complete Set of Genomic Binding Location at Single Base Accuracy The genomic ChIP-exo method described herein overcomes the resolution and false discovery limits of current genome-wide mapping methods. As an example, a full description of its implementation and validation with one factor, the *Saccharomyces cerevisiae* sequence-specific transcription factor Reb1, is provided herein. Equivalent statistics have been achieved with other factors (e.g., those listed in Example 1).

Figure 2A:
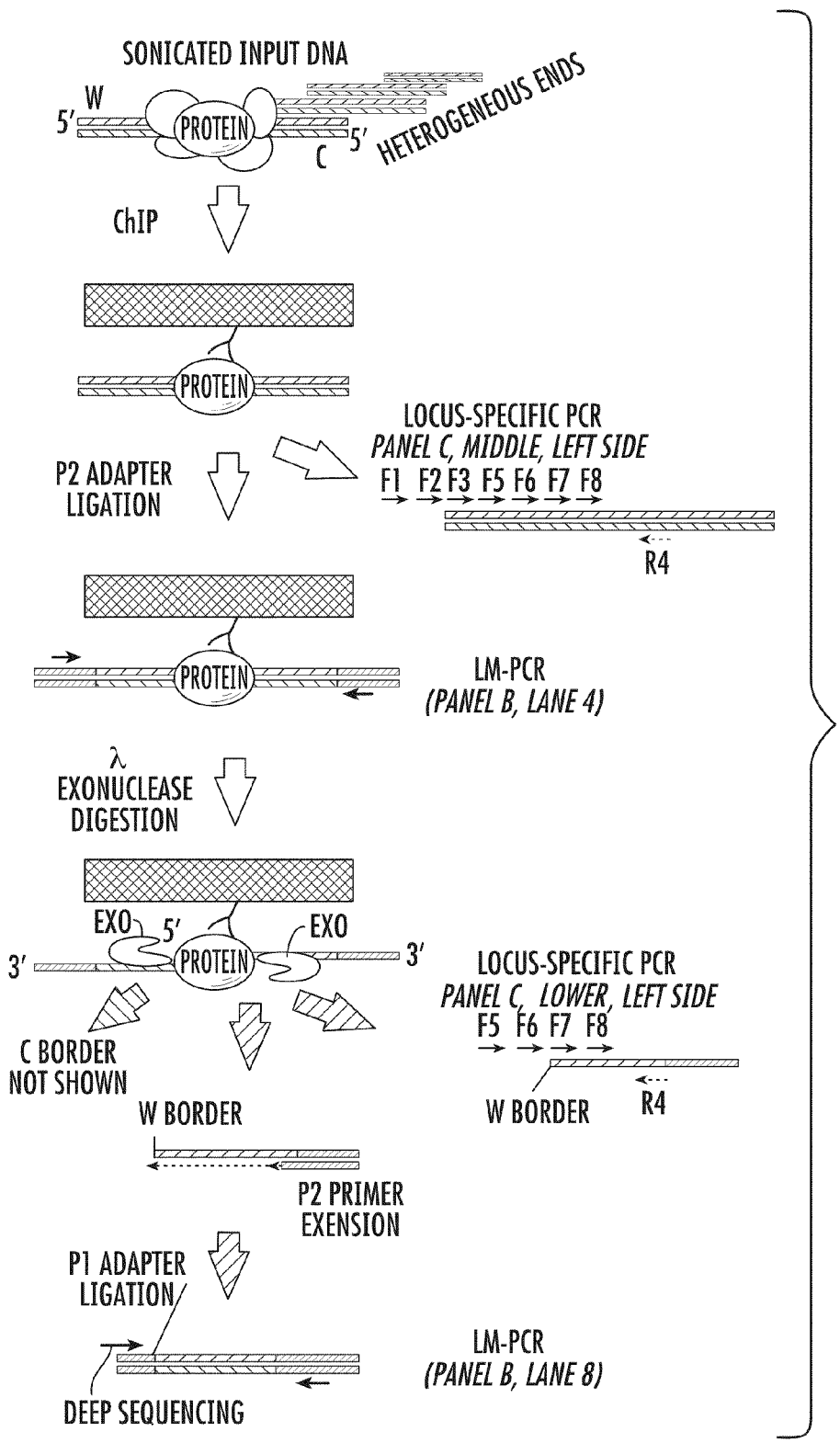
FIG. 2 is a schematic illustration of ChIP-exo and a series of photographs of electrophoretic gels and plots showing locus-specific validation. (A): Overview of the ChIP-exo procedure. Cells are crosslinked with formaldehyde, sonicated, and immunoprecipitated (ChIP). Because of the inefficiency of formaldehyde crosslinking and the stringency of the immunoprecipitation step, neighboring proteins of the target protein are noncovalent and washed away during ChIP. While still on the resin, each end of the ChIP DNA is ligated to sequencing adaptor (e.g. the P2 adaptor), then digested with lambda exonuclease until blocked by a protein-DNA crosslink. The DNA is eluted, the crosslink reversed, and the DNA converted to double-stranded DNA. A second sequencing adaptor (e.g., P1) is then ligated to the filled-in end, which marks the site of the exonuclease digestion barrier when subjected to deep sequencing. (B): LM-PCR detection of TFIIB (Sua7-TAP) and BY4741 ChIP DNA. In this example, BY4741 is a negative control that lacks the TAP tag. Lane 5 lacks template DNA in the PCR. ChIP DNA was amplified using primers against ligated adapters (and thus is not locus-specific), then was electrophoresed on a 2% agarose gel and stained with ethidium bromide. (C): Locus-specific PCR at the RPL3 promoter. Upper, middle, and lower panels display PCR results from input genomic DNA, standard sonicated Sua7-ChIP DNA, and Sua7-ChIP-exo DNA, respectively. Primers specific to the RPL3 promoter were arranged as illustrated in panel A right side as "locus-specific PCR". PCR primer sequences are listed in Supporting Online Material. (D): Quantification of the ChIP-exo signal for RPL3 (upper panel) using locus-specific PCR. For RPL5 (lower panel), the W border was placed between −107 and −87 by from the RPL5 ORF start. The C border was narrowed to a range of −93 to −85 bp. The midpoints of each range (−97 and −89) defined the W and C borders, respectively, of an 8 by region at RPL5 that is bound by TFIIB. All PCR signals were normalized to input.

In an effort to increase genomic mapping resolution and drastically reduce background DNA contamination, the fact that a protein-DNA crosslink, the cornerstone of ChIP, creates an impediment to exonuclease digestion was exploited (FIG. 2A). Specifically bound factors will impose digestion limits at precise locations in the genome, whereas contaminating nonspecific DNA, which is not crosslinked to the immunoprecipitated factor, is expected to be largely degraded, and thus eliminated from detection. A primary aspect of ChIP-exo is the use of a double-stranded-specific exonuclease, such as lambda ($\lambda$) exonuclease, that degrades one of the complementary DNA strands into mononucleotides in the 5'-3' direction until it reaches the protein-DNA crosslink (FIG. 2A). Another advantage of using lambda exonuclease is that it lacks sequence cleavage bias that is inherent in the use of MNase, DNaseI, and sonication to fragment DNA. Nonetheless, as mentioned above, exonucleases that digest DNA in a 3'-5' direction can also be used. Use of nucleases that digest both strands would not be productive, as they result in near complete digestion of the bound DNA, leaving insufficient DNA to uniquely identify the bound target sequence.

Formaldehyde crosslinking of proteins to DNA is inefficient (typically <0.1% at any one site), and the stringency of the immunoprecipitation step removes all but covalently crosslinked adducts and the antigen/antibody complex (illustrated in FIG. 2A). Therefore, the exonuclease barrier is unlikely to be created erroneously by nearby bound proteins (and the evidence presented here bears this out), as they will be stripped away prior to exonuclease treatment.

Locus-specific PCR or deep sequencing can be used to detect the site of the $\lambda$ exonuclease barrier on one strand versus the other (illustrated in FIG. 2A), the latter by separately tagging the digested blocked end with a DNA sequencing adaptor, and the undigested sonicated end with a different DNA sequencing adapter. Moreover, as useful criteria for identifying bound locations, the $\lambda$ exonuclease barrier on each side of the crosslinked factor is expected to reside at a fixed distance from each other, with the "W" or "+" strand border being at a lower coordinate than the "C" or "−" strand border (because coordinates on the W/+strand are numbered in the same order as the directionality of $\lambda$ exonuclease digestion).

Figure 2B:
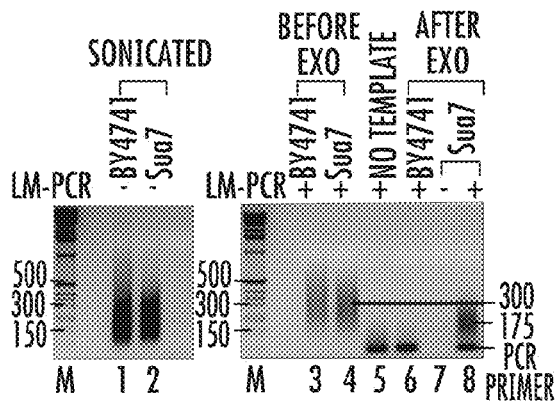

As an initial proof-of-principle, locus-specific ChIP-exo was performed on the general transcription factor TFIIB/Sua7, because it crosslinks efficiently to DNA (Koerber et al., Mol Cell vol. 35:889, 2009). Sonicated ChIP DNA from TAP-tagged TFIIB and the untagged negative control BY4741 ranged from 100-400 by before immunoprecipitation and exonuclease treatment (FIG. 2B, lanes 1-2). Using an LM-PCR (ligation-mediated PCR) assay, both were detected after immunoprecipitation (lanes 3-4) because the vast majority of ChIP DNA consists of nonspecific contamination which is detectable by LM-PCR. However, 2 exonuclease removed nearly all contaminating nonspecific DNA (lane 6 vs 8), and reduced the DNA sizes by half (lane 4 vs 8).

Figure 2C:
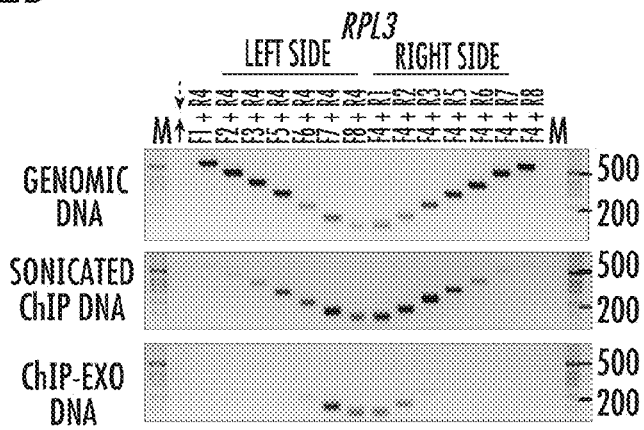
Figure 2D:
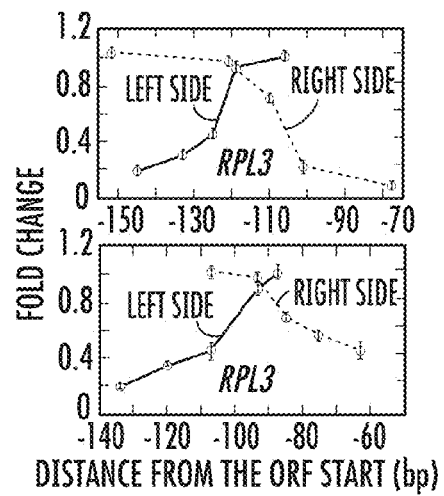

Using locus-specific PCR, the W and C borders of TFIIB were initially mapped at low resolution using broadly spaced primers directed at two highly expressed ribosomal protein genes (RPL3 and RPL5), and both were compared against standard ChIP (FIG. 2C). Standard ChIP (second panel) placed the W end of the ChIP DNA fragments broadly between −383 and −226 by from the RPL3 ORF start, as expected of the randomly fragmented ChIP DNA, whereas the ChIP-exo trimmed material (third panel) had W ends detected more narrowly between −169 and −106 by (methodology described below). Using closely spaced primers, this end was further narrowed to a range of −125 to −119 by (FIG. 2D) (methodology described below). Mapping of the C strand in the same way placed the C border between −121 and −101. The midpoints of each range (−122 and −110) defined the W and C borders, respectively, of a 12 by region at RPL3 that is bound by TFIIB. Consistent with this placement, the RPL3 TATA box, to which the TBP/TFIIB complex binds, is centered at −113. Thus, ChIP-exo can be used to define the precise location of a transcription factor at a single location using PCR.

The main potential of ChIP-exo resides in coupling it to genome-wide sequencing technologies (illustrated in FIG. 2A), where the precise exonuclease barrier from crosslinking can be identified. Since DNA sequences downstream of the exonuclease stopping point remain intact, sequencing can proceed as far as needed for unique identification. Since only the 5' end of each single-stranded DNA product of ChIP-exo defines the $\lambda$ exonuclease border, it must be demarcated from the other (3') end that is generated by sonication (FIG. 2A). Thus, it was important to initiate construction of the ChIP library on the resin, by ligating a DNA sequencing adaptor (P2) prior to $\lambda$ exonuclease treatment, so as to mark the sonicated end, then complete library construction after $\lambda$ exonuclease treatment using a different DNA sequencing adaptor (P1) to mark the exonuclease barrier (methodology described below). The solid phase components of this procedure had the added benefit of greatly facilitating library construction through the multiple enzymatic steps, by simply washing the resin and adding the next reaction mix.

Figure 3A:
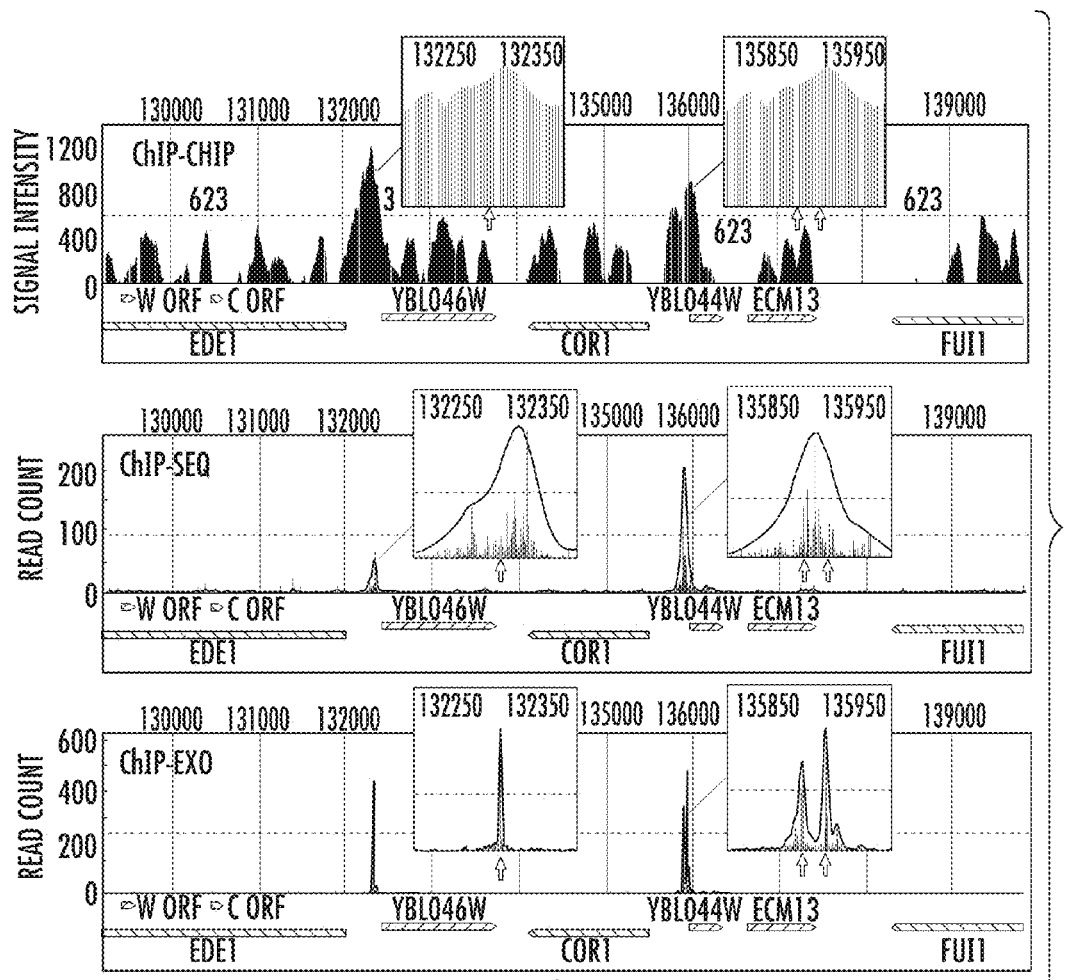

ChIP-exo was performed on the sequence-specific DNA binding protein Reb1, whose location could be independently validated from its cognate DNA recognition sequence (TTACCCG) (Morrow et al., J Biol Chem 264:9061, 1989; Harbison et al., Nature vol. 431:99, 2004). ChIP-exo samples were subjected to DNA sequencing (ABI SOLiD, although other platforms could be employed) (Table 4). Standard (no exonuclease treatment) Reb1 ChIP samples were also sequenced, whose positional resolution was enhanced by size selection (50-130 bp) (methodology described below), and compared the results to an existing Reb1 ChIP-chip (Affymetrix, 5 by probe spacing) dataset (Venters and Pugh Genome Res vol. 19:360, 2009). Example comparisons at the YBL046W and YBL0441F loci are shown in FIG. 3A (see FIG. 6 for other loci (Albert et al., Bioinformatics vol. 24:1305, 2008)).

Figure 3B:
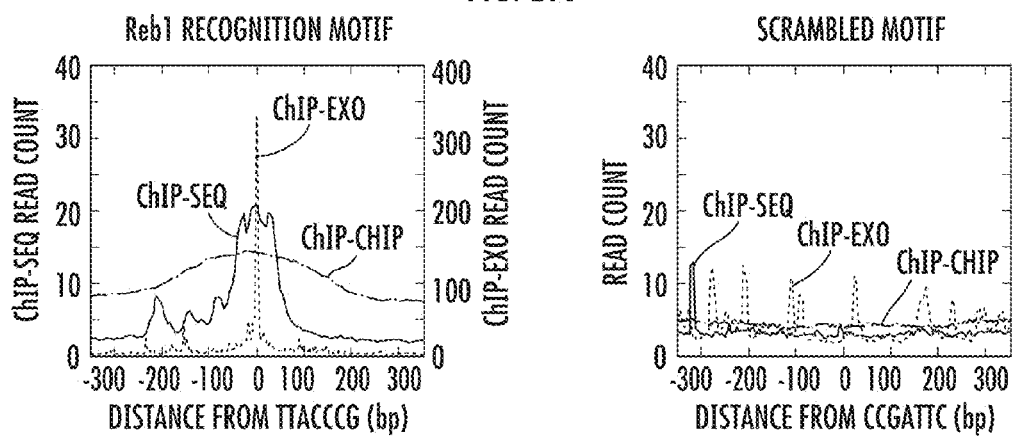

Frequency distribution plots of all unfiltered ChIP-chip, ChIP-seq, and ChIP-exo data around all 791 TTACCCG motifs in the yeast genome, and 771 control scrambled sites (CCGATTC) are shown in FIG. 3B. As seen at individual sites, for ChIP-exo a sharp spike of tags was centered over the TTACCCG motif midpoint, but not over the scrambled motif. For ChIP-chip and ChIP-seq, the distribution was much broader, resulting in substantially decreased mapping certainty. Also higher background DNA contamination in comparison to ChIP-exo was evident. Lower background DNA results in fewer false positives, fewer false negatives, and fewer tags (by a factor of at least 100) needed to cover all bound locations.

Figure 4A:
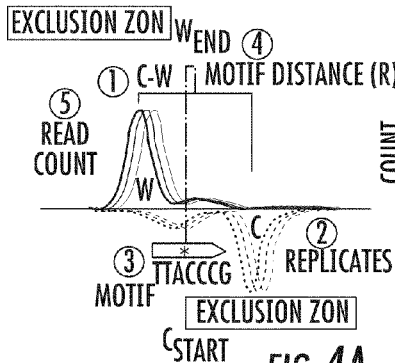
Figure 4B:
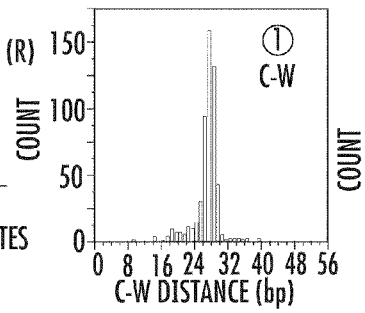
Figure 4C:
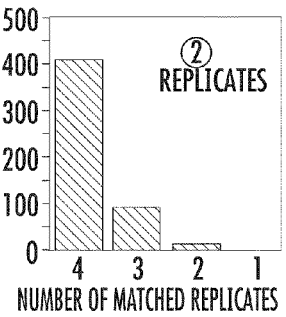

Evaluation of binding criteria for Reb1. To identify an essentially complete set of bound locations, five primary criteria were considered: 1) measured site size (distance between W and C strand borders), 2) biological replicates, 3) binding motif sequence, 4) distance from motif, and 5) occupancy level (FIG. 4A, methodology described below). These criteria are applicable to equivalent studies with other proteins. Each of these five criteria was set to have stringent and relaxed limits (Table 5). The relaxed limits were set to nominal values which served to eliminate spurious relationships. The stringent limits were used only to evaluate individual criteria.

The five criteria were individually evaluated by obtaining putative bound locations meeting a specified four of the five stringent criteria, and plotting a frequency distribution of values associated with the fifth criteria (FIG. 4B-F). Since Reb1 plays regulatory roles, some positive and some negative, in telomere length maintenance, DNA replication, and transcription by RNA polymerase I and II, genomic regions associated with each of these processes were examined separately. From the analysis shown in FIG. 4, the following remarkable statistics were obtained for Reb1-bound locations in the RNA polymerase II transcribed portions of the genome: Panel B—a binding site size of 27 by (including tolerance for lambda exonuclease "headroom"); Panel C—97% identified in at least 3 out of 4 replicates, Panel D—64% utilizing a TTACCCG binding motif (83% using TTACCCK and the rest employing other single nucleotide variants); Panel E—most significantly, 89% of the bound locations within 1 by of the motif midpoint (97% within 4 bp); and Panel F—an average read count (occupancy level) that was >2000 times the average background DNA signal. The standard deviation of bound locations from TTACCCG motifs for ChIP-exo was ±0.26 bp, which was one hundred fold less than for a parallel ChIP-seq experiment (FIG. 7).

Figure 4D:
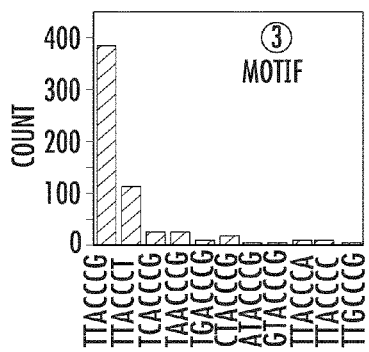
Figure 4E:
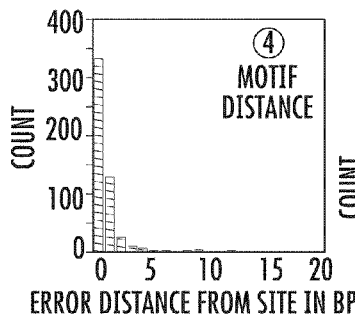
Figure 4F:
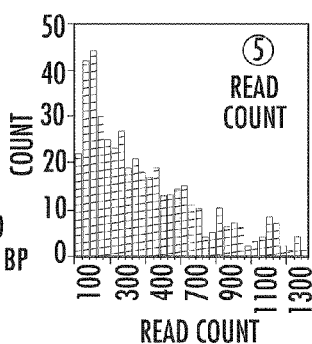
Figure 4G:
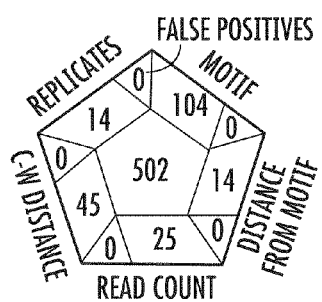
Figure 4H:
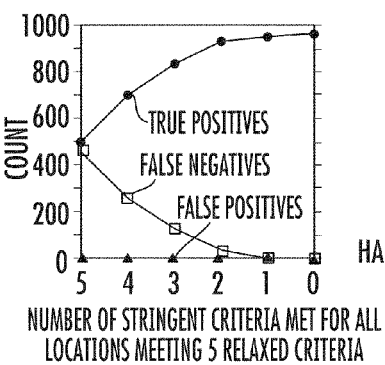
Figure 4I:
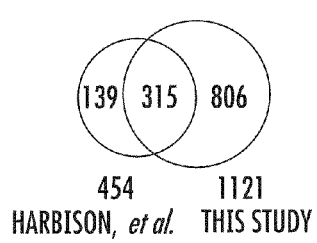

A total of 502 Reb1-bound locations met all five stringent criteria, and a total of 704 bound locations met at least four of the five stringent criteria (FIG. 4G). As more criteria were allowed to meet the relaxed rather than the stringent limit, the total number of bound locations leveled off at 964 (FIG. 4H). This leveling off indicates that few or no false negatives remain undetected in the analyzed regions of the genome. Including other regions of the genome, 1093 Reb1-bound locations were detected, including an additional 89 at telomeres, 22 at tDNA, 8 at rDNA, and 10 at replication origins (ARS), which is 2-3 times previous estimates (Hesselberth et al., Nat Methods vol. 6:283, 2009; Harbison et al., Nature vol. 431:99, 2004). The overlap between the genes associate with this determined set and that determined previously (Harbison et al., Nature vol. 431:99, 2004) is shown in FIG. 4I and FIG. 8.

To calculate the false positive rate, the same analyses were rerun using a scrambled recognition motif. This was repeated multiple times ensuring that the scrambled motif did not represent a degenerate version of the original motif. An average of 0.42 bound false positives out of 964, was determined (Table 6). Additionally, when false positives were determined by performing ChIP-exo on different proteins, zero locations met all five relaxed Reb1 criteria. From this, it can be concluded that for at least Reb1, ChIP-exo produces essentially zero false positives.

Figure 9A:
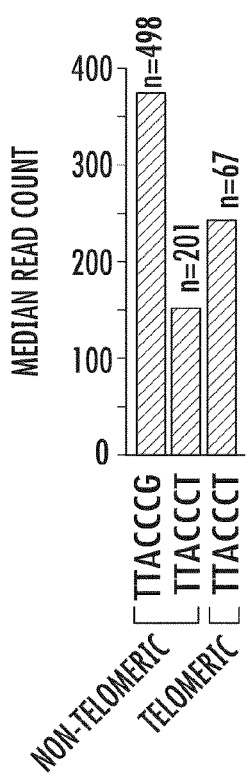
Figure 9B:
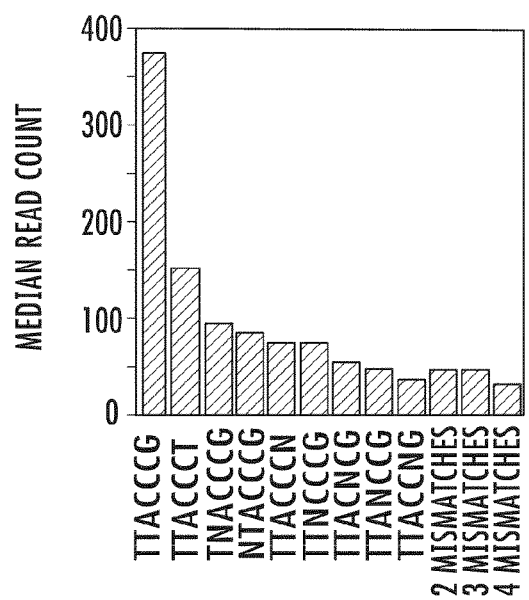

Telomeric-bound Reb1 displayed essentially all the properties of Reb1 bound elsewhere, except that it had a nearly exclusive preference for a single base motif variant: TTACCC T. Thus, whether Reb1 utilizes one motif or the other depends upon where in the genome that motif resides. Quantitative in vitro binding studies suggest that differential affinities for TTACCC(G) vs (T) might arise from the sequence environment in which they reside, but such a notion has not been considered on a genomic scale. Consistent with genomic context being important, the highly utilized TTACCCG motifs had higher occupancy (read count) than the lesser-utilized TTACCCT motif (FIG. 9B). However, the highly utilized telomeric TTACCCT sites exhibited substantially higher occupancy levels (FIG. 9A). Thus, genomic context may influence not only what sequence motif a protein might use, but also its occupancy level.

Genomic regions such as tDNA, rDNA, and ARS had essentially the same properties of Reb1 bound to the majority of the genome, except that they had a preference for sequence motifs with 1-2 mismatches, which provides further evidence for context-dependent motif utilization.

Genomic properties of Reb1. Essentially all TTACCCG motifs, whether Reb1-occupied (498 sites) or unoccupied (247 sites), were located in a narrow region centered at −95 by from the transcription start site (TSS) (FIG. 5A), and were nucleosome free. Their precise location relative to the TSS and their virtual absence in the rest of the genome suggest that even unbound sites may be functional under different circumstances, and that the TTACCCG motif and location are under considerable evolutionary constraint.

Figure 5A:
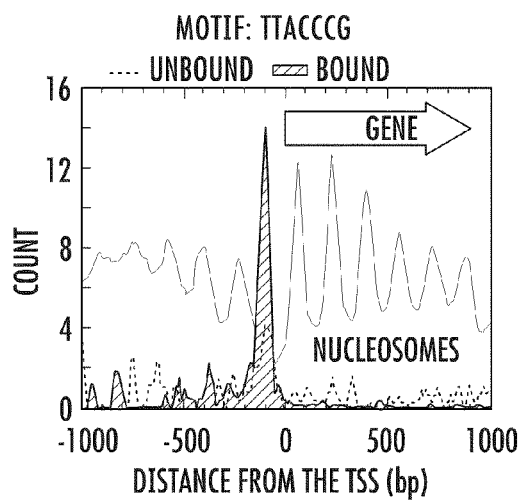
Figure 5B:
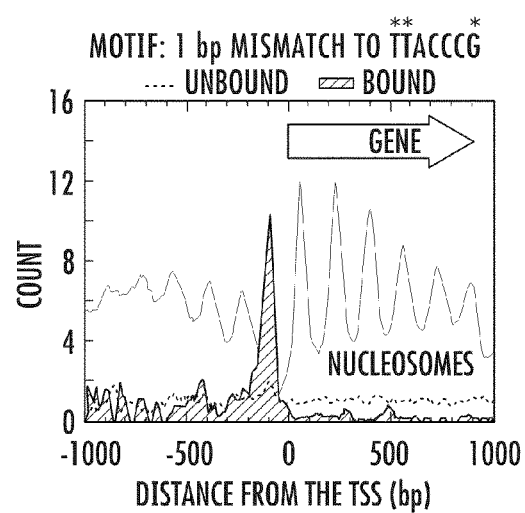

Essentially all Reb1-bound "relaxed" variants of the TTACCCG motif (Table 5) were located in nucleosome-free promoters as well, and centered at −95 by from the TSS (FIG. 5B). Unlike the TTACCCG motif, unbound versions of relaxed variants were randomly scattered throughout the genome, suggesting that they are not under evolutionary selective pressure, perhaps because they have lower affinity for Reb1. Indeed, motifs that were used less often in the genome had lower Reb1 occupancy levels (FIG. 9B), and also have less affinity for Reb1 in vitro (Wang and Warner Mol Cell Biol vol. 18:4368, 1998; Biswas and Bastia Mol Cell Biol vol. 28:6844, 2008).

Figure 5C:
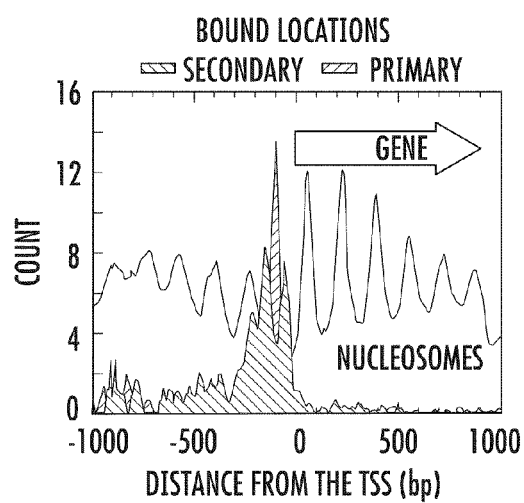
Figure 5D:
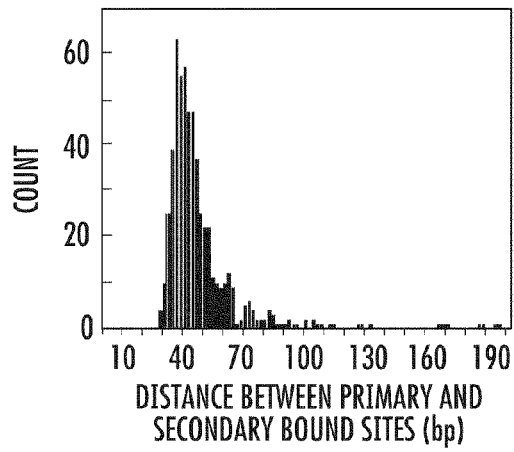

An additional 690 locations were identified that barely met relaxed criteria 1, 2, and 5 (Table 5), and lacked a recognizable motif. Remarkably, >90% of these "secondary" sites were located ~40 by from a previously identified "primary" bound location, either upstream, downstream or both (FIGS. 5C and 5D). Occupancy at these secondary sites was low (<5% of primary sites), and may reflect local contacts from primary bound Reb1, perhaps as a dimer. Alternatively, it could reflect interactions with a different bound factor that crosslinks to Reb1 (albeit inefficiently) such as a nucleosome, whose border indeed resides ~40 by from primary Reb1 sites. Reb1 is well-known to organize NFRs and nucleosome boundaries (Hartley and Madhani Cell vol. 137:445, 2009).

ChIP-exo is the first technique that has the potential to reveal essentially a complete and unambiguous set of genomic binding locations at the single by limit of resolution, and thus allows for a more complete assessment of its regulatory network. When placed in the context of other factors mapped at the same resolution, the arrangement of these factors along the one-dimensional promoter lattice may be determined, and this should provide greater insight into transcription factor organization at promoters. Its single-base accuracy removes substantial ambiguity in identifying cognate recognition motifs and binding site size in the genome, and this should allow a clearer understanding of the relationship between motif properties (sequence and positioning) and factor occupancy. Improved mapping accuracy and background reduction from nuclease digestion has the practical benefit of substantially reducing mapping costs, particularly for complex genomes, where >99% of the sequencing reads represent background.

Materials and Methods

The Reb1 TAP-tagged *Saccharomyces cerevisiae* strain is a BY4741 derivative obtained from Open Biosystems. Cells were grown in 250 ml of yeast peptone dextrose (YPD) media at 25° C. to an $OD_{600}$=0.8. Formaldehyde was added to a final concentration of 1% for 15 min, then quenched with 0.125 M glycine. Cells were harvested by centrifugation, disrupted with glass beads at 4° C. with by vortexing on high for 2 hr.

Before ChIP-exo sample were subjected to SOLiD sequencing, the W strand and C strand borders of ChIP-exo sample were mapped using locus-specific PCR (FIG. 2A). For this purpose, TFIIB (Sua7) TAP-tagged *Saccharomyces cerevisiae* strain was used instead of Reb1 TAP-tagged strain and followed the same procedure as described above until PCIA extraction and ethanol precipitation without P2 adaptor ligation. PCR products were electrophoresed on a 2% agarose gel and stained with ethidium bromide. For comparison, locus-specific PCR of genomic DNA and standard ChIP sample was performed using the same PCR primers.

ChIP-seq sample was prepared by following the same procedure as described above until immunoprecipitation and washing with FA-lysis buffer, FA High Salt buffer, FA Wash 2 buffer, and FA Wash 3 buffer. The immunoprecipitated samples were then eluted in 450 ul of ChIP Elution buffer (0.5% SDS, 25 mM Tris, 2 mM EDTA pH 8.0, 0.2 M NaCl) at 65° C. for 15 min. Crosslinks were reversed and proteins were removed by incubation with 1.5 ul Proteinase K (Roche, 20 mg/ml) at 65° C. for 6-16 hr. Samples were extracted with Phenol:Chloroform:Isoamyl alcohol (PCIA) and precipitated with ethanol. Samples were resuspended in 10 ul water and polished with 0.5 U T4 DNA polymerase (New England Biolabs), 100 uM dNTPs, in 20 ul 1×NEBuffer 2 at 12° C. for 20 min. After end polishing, samples in 20 ul of 1×NEBuffer 2 were ligated with 22.5 pmol of P1 adaptor (sequence as described above) and 22.5 pmol of P2 adaptor (sequence as described above), 1500 U T4 DNA ligase in additional 60 ul 1× T4 ligase buffer at 25° C. for 60 min. Samples were then purified over Agencourt AMPure magnetic beads (Beckman Coulter Genomics) by following the manufacturers instructions, and PCR amplified with PCR primers (sequences as described above), 2 U Taq DNA polymerase (GeneChoice) and 1 U PfuTurbo DNA polymerase (Stratagene), 250 uM dNTPs in 40 ul 1× Taq DNA polymarase PCR Buffer (GeneChoice). PCR cycles were minimized by checking PCR products on 2% agarose gel every three PCR cycles until amplified PCR signals were detected (e.g. 15, 18, 21, and 24 cycles). 50-130 by PCR products were gel-purified from 2% agarose using Qiaquick gel purification columns (Qiagen). Purified samples were quantified using 2100 Bioanalyzer (Agilent) and sequenced using the SOLiD genome sequencer (Applied Biosystems) in accordance with the manufacturers instructions.

Chromatin pellets were generated by centrifugation, and were resuspended with 0.75 ml of FA-lysis buffer (150 mM NaCl, 1% triton X-100, 50 mM HEPES, 2 mM EDTA, 0.1% sodium deoxycholate) with 0.1% SDS, and centrifuged. This wash was repeated two times. Chromatin pellets were sonicated using a Biorupter (Diagenode, power: high, time: 30 sec on/30 sec off for 30 minutes). Solubilized chromatin was then diluted with FA-lysis buffer to an SDS concentration of 0.05%, incubated with 20 ul bed volume of IgG-bound sepharose resin at 4° C. for 1.5 hr with mixing. Immunoprecipitated samples were then washed successively with 1 ml of FA-lysis buffer, FA High Salt buffer (1 M NaCl), FA Wash 2 buffer (0.5 M NaCl), and FA Wash 3 buffer (0.25 M LiCl).

While still on the resin, the immunoprecipitated DNA was subjected to enzymatic reactions, within intermittent mixing, in the following order. 1) End polishing: 4.5 U T4 DNA polymerase (New England Biolabs), 100 uM dNTPs, in 50 ul 1× NEBuffer 2 at 12° C. for 30 min, 2) P2 adapter ligation: 150 pmol P2 adapter (modified from the sequence provided by Applied Biosystems: 5' OH-AGAGAATGAGG-OH (SEQ ID NO:5) 3', 5' Phos-AACTGCCCCGGGTTCCTCAT-TCTCT-OH (SEQ ID NO:6) 3', oligos synthesized by Integrated DNA Technologies, purified by standard desalting), 1250 U T4 DNA ligase (gift of S. Tan of this department) in 40 ul 1× T4 ligase buffer at 25° C. for 60 min. For barcoded P2 adaptor (ChIP-exo replicate 2, Table 4), sequence was modified from the sequence provided by applied Biosystems: 5' OH-CGCCTTGGCCGTACAGCAG GGGCTTNNNNAGAGAATGAGGAACCCGGGGCA GTT-OH (SEQ ID NO:7) 3', 5' Phos-CTGCCCCGGGTTC-CTCATTCTCTNNNN AAGCCCCTGCTGTACGGCCAAGGCG-OH (SEQ ID NO:8) 3', underline sequences indicate barcode shown on Table 4, bold sequences indicate a statistical code for PCR bias check), synthesized and followed by same procedure as the P2 adaptor ligation. 3) Nick repair: 15 U phi29 polymerase (New England Biolabs), 150 uM dNTPs in 40 ul 1× phi29 reaction buffer (New England Biolabs) at 30° C. for 20 mM. 4) Lmabda exonuclease: 10 U lambda exonuclease (New England Biolabs) in 1× lambda exonuclease reaction buffer (New England Biolabs) at 37° C. for 30 min (S1, S2). 5) $RecJ_f$ exonuclease: 30 U $RecJ_f$ exonuclease (New England Biolabs) in 1× NEBuffer 2 at 37° C. for 30 min. Between each reaction the resin was washed sequentially with the following buffers in order: a) 10 mM Tris-EDTA Buffer (1 mM EDTA, pH 8.0), b) FA High Salt Buffer, c) FA Wash 2 Buffer 3, d) 10 mM Tris-Cl (pH 8.0, pH 7.5, or pH 9.5 depending on the next enzymatic step).

ChIP-exo treated DNA was eluted with 500 U TEV protease (Invitrogen) in 500 ul TEV Elution buffer (100 mM Tris-Cl pH 8.0, 100 mM NaCl, 10% glycerol, 0.1% IGEPAL, 0.5 mM EDTA) with 0.1% 2-mercaptoethanol at 25° C. for 2 hr. Alternative SDS-based elution methods should be equally effective. Crosslinks were reversed and proteins were removed by incubation with 1.5 ul Proteinase K (Roche, 20 mg/ml) at 65° C. for 6-16 hr. Samples were extracted with Phenol:Chloroform:Isoamyl alcohol (PCIA) and precipitated with ethanol. Samples were resuspended in 20 ul water, and incubated with 5 pmol P2 primer (modified from the sequence provided by Applied Biosystems: 5' OH-CTGC-CCCGGGTTCCTCATTCTCT-OH (SEQ ID NO:9) 3', oligos synthesized by Integrated DNA Technologies, purified by standard desalting) in 20 ul 1× phi29 reaction buffer at 95° C. for 5 min., then 63° C. for 5 min., then 30° C. for 2 min. 10 U of phi29 polymerase and 20 uM dNTPs were added and incubated at 30° C. for 20 min., followed by a heat inactivation at 65° C. for 10 min. 15 pol of P1 adapter (sequence provided by Applied Biosystems: 5' OH-TCTC-TATGGGCAGTCGGTGAT-OH (SEQ ID NO:10) 3', 5' OH-ATCACCGACTCCCCATAGAGAGG-011 (SEQ ID NO:11) 3', oligos synthesized by Integrated DNA Technologies, purified by standard desalting) and 1000 U T4 DNA ligase were added to a final volume of 80 ul in 1× T4 ligase buffer, and incubated at 25° C. for 60 min, followed by heat inactivation at 65° C. for 10 min. For barcoded P2 adaptor (ChIP-seq replicate 1, ChIP-exo replicate 1, 3, and 4, Table 4), sequence was modified from the sequence provided by applied Biosystems: 5' OH-TCTCTATGGGCAGTCGGTGATAGCG-OH (SEQ ID NO:12) 3', 5' OH-CGCTATCACCGACTGCCCATAGAGAGG-OH (SEQ ID NO:13) 3', underline sequences indicate barcode shown on Table 4) and synthesized and followed by same procedure as P1 adaptor ligation.

Samples were then purified over Agencourt AMPure magnetic beads (Beckman Coulter Genomics) by following the manufacturers instructions, and PCR amplified (sequence provided by Applied Biosystems:
5' OH-CCACTACGCCTCCGCTTTCCTCTC-TATGGGCAGTCGGTGAT--OH (SEQ ID NO:14) 3',
5' OH-CTGCCCCGGGTTCCTCATTCT-OH (SEQ ID NO:15) 3', oligos synthesized by Integrated DNA Technologies, purified by standard desalting) with 2 U Taq DNA polymerase (GeneChoice) and 1 U PfuTurbo DNA polymerase (Stratagene), 250 uM dNTPs in 40 ul 1× Taq DNA polymarase PCR Buffer (GeneChoice). PCR cycles were minimized by checking PCR products on 2% agarose gel every three PCR cycles until amplified PCR signals were detected (e.g. 15, 18, 21, and 24 cycles). 120-160 by PCR products were gel-purified from 2% agarose using Qiaquick gel purification columns (Qiagen). Purified samples were quantified using 2100 Bioanalyzer (Agilent) and sequenced using the SOLiD genome sequencer (Applied Biosystems) in accordance with the manufacturers instructions.

Use of a blend of lambda exonuclease and $RecJ_f$ reduces background DNA contamination. Residual uncrosslinked fragments that escape degradation are expected to be randomly distributed throughout the genome. As λ, exonuclease digests one strand of the double-stranded DNA, the other strand is rendered resistant to this exonuclease. Therefore, a 5'-3' single-strand specific exonuclease ($RecJ_f$) was also added, to diminish this background.

The expectation is that each sequence tag corresponds to a separately measured binding event. However, because the ChIP DNA is PCR amplified prior to identification, there is a possibility that the same ChIP DNA molecule may be detected multiple times. This may be problematic for quantifying transcription factor occupancy levels, if certain DNA molecules are preferentially amplified over others. Two "built-in" detectors of such clonal molecules are provided. Step 1: only those tags whose 5' ends have identical genomic coordinates (and strand) are clonal candidates. Step 2: for some samples the library primers were designed to contain random nucleotides at 3' consecutive positions (termed a statistical code, Table 4). These positions are individually sequenced along with the ChIP DNA and are expected to be unique for individually sampled events (or at least statistically proportioned in the same way as the entire dataset). Thus, any clonal candidate identified in step 1 that has the same statistical code as an existing tag (having the same genomic coordinate and strand) is removed. This statistical code did not exist for some samples and thus was not applied. Essentially identical results were obtained with or without use of the statistical code.

Alignment to genome and data sharing. The *Saccharomyces* reference genome was obtained. The entire length of the 31-35 by reads depending on location of barcodes were aligned to the reference genome using Corona Lite software provided by the SOLiD system up to 3 mismatches. This process was repeated for the remaining tags, after removal of the 3' most 6 bp, which tend to have higher error rates. Raw tags are available at NCBI Trace Archives. Processed data (the set of bound locations) can be found in Table 4. Raw tags mapped to genomic coordinates and annotated features can be queried at the Penn State Genome Cartography website. For purposes of display in the browser, the coordinates of the 5' end of all W strand tags are shifted to a higher coordinate by D/2 (defined below), and the 5' end of all C strand tags are shifted to a lower coordinate by D/2.

GeneTrack was used to plot the genomic location of the 5' ends of each tag in the yeast genome (S3). GeneTrack was used to separately identify peaks on the "+" (W) and "−" (C) strand. (W and C are used here to avoid confusion with arithmetic symbols). GeneTrack replaces each tag with a probalistic, distribution of occurrences for that tag at and around its mapped genomic coordinate. The distance decay of the probalistic distribution is set by the user by adjusting the parameter termed "sigma" (i.e. the standard deviation of the idealized distribution). GeneTrack then sums the distribution over all mapped tags. This results in a smooth continuous trace that can be globally broadened or tightened by adjusting sigma. GeneTrack starts with the highest smoothed peak first, treating each strand separately if indicated by the data, then sets up a user-defined exclusion zone of width D (defined below) that is centered over the peak. The exclusion zone prevents any secondary peaks from being called on the same strand within that exclusion zone. GeneTrack continues through the data in order of peak height, until no other peaks are found. In principle, the width of the exclusion zone may be as large as the DNA region occupied by the native protein plus a steric exclusion zone between the protein and the exonuclease. On the other hand the site might be considerably smaller if the protein is in a denatured state during exonuclease digestion. GeneTrack continues with peak identification until no more peaks have been identified. GeneTrack outputs "chrom" (chromosome number), "strand" (+/W or −/C strand), "start" (lower coordinate of exclusion zone), "end" (higher coordinate of exclusion zone), and "value" (peak height).

Sigma and width (D) in GeneTrack was determined. In general, higher resolution data or smaller binding site size data should use smaller sigma values. (large binding site size data such as 147 by nucleosomal DNA use a larger sigma value like 20). Too high of a sigma value may merge two independent nearby binding events. This may be desirable if closely bound factors are not distinguishable. Too low of a sigma value will cause some tags that contribute to a binding event to be excluded, because they may not be located sufficiently close to the main peak. If alternative (mutually exclusive) binding is expected for two overlapping sites, and these sites are to be independently recorded, then an empirically determined smaller exclusion zone width is set. Thus the value of sigma is set empirically for each mapped factor, depending upon the resolution and binding site size of the binding event.

For transcription factors mapped by ChIP-exo, sigma should initially be set at 5, and width set at 20. Sigma was then varied between ~3 and ~20 and inspected in the GeneTrack browser for empirical assessment of optimal peak capture vs. background exclusion. Determination of the optimal exclusion zone width was largely independent of sigma and number of peaks used. 2000 peaks with the highest read counts for each W and C peak (total 4000 peaks) (nominally 3-10 times the number of expected bound locations) were chosen. The distances between adjacent W and C peaks ($Width_{initial}$-$W_{end}$+$C_{start}$) were then compiled into a frequency distribution plot (exemplified by FIG. 4B). The mode of this C-W frequency plot is defined as "D", after rounding to the nearest odd integer (since the midpoint should be an integer). The standard deviation ($\sigma_D$) of D is also determined, using those values that reside in an apparent normal distribution around D. D and $\sigma_D$ are dataset specific (although they should essentially be the same for each replicate dataset), and thus should be determined separately for each replicate. GeneTrack is then re-run using the determined value for sigma and width.

Pre-filter data was obtained. The purpose of pre-filtering is to remove the vast amount of nonspecific background peaks without losing true peaks, so as to enhance computational efficiency. To determine the pre-filtering cutoff, the read counts per peak were modeled as a poisson distribution, and a cutoff was set in which the probability of removing false negatives was zero (the probability of including all possible positives was 100%).

Criterion 1 involves matched peak pairs. W and C peaks corresponding to the left (W peak) and right borders (C peak) of putatively bound locations were match paired with a W peak matched with its closest downstream C peak in which the respective exclusion zone coordinates $C_{start}$-$W_{end}$ met relaxed criterion 1 ($\leq$D, Table 5), which essentially sets a maximal peak-to-peak tolerance at twice the genome-wide mode (FIG. 4B) of the distance from W peak to closest C peak. This was facilitated by creating a Reference Coordinate equal to (100+chromosome number)*$10^7$+$W_{end}$ (or $C_{start}$) coordinate for each exclusion zone. The Reference Coordinate for matched pairs was determined to be the average of the two $W_{end}$ and $C_{start}$ Reference Coordinates. Unmatched exclusion zones were discarded. The use of a relaxed criterion was implemented to catch nearby outliers that by other criteria might be considered true binders. One might expect such nearby outliers to arise if a subset of bound sites also contained another bound protein, and thus producing an alternative border (block to exonuclease). However, the inefficiency of formaldehyde crosslinking (typically <0.1%) coupled to denaturing ChIP conditions precludes retention of neighboring bound proteins (FIG. 7, 8), and so this concern does not materialize. When resin-bound ChIP material is prepared for exonuclease digestion it is possible that none, some, or all of the protein will refold onto the DNA. Consequently, borders will be generated to varying extent by the crosslink itself (denatured case) or by steric blocks from the refolded protein.

Criterion 2 involves replicates. Multiple independent biological replicates were performed for each experiment (four for Reb1). Replicates of putatively bound matched peak pairs were assigned to each other based upon the closest Reference Coordinate, with a maximum nominal allowance of D/2 by apart for any two pairs. Thus, a replicate location belonged to a given consensus binding location if it resided $\leq$D/2 by from any other member of that location. A single Consensus Reference Coordinate (CRC) was created for the consensus location by computing the median Reference Coordinate for the replicates belonging to that consensus location (fractional coordinates were not rounded). A CRC in which $\geq$50% of the replicates were present (i.e., two out of four replicates for Reb1, see FIG. 4C) was retained in the dataset. Those present in >70% of the datasets were marked as meeting stringent criterion 2 ("s") the rest were marked as meeting relaxed ("r") criteria 2 (Table 5).

Read count normalization was performed. The read count for a given bound location is expected to vary between datasets due to differences in sequencing depth of coverage. In each dataset, read counts per bound location were normalized to the median read count of most likely bound sites in a dataset (i.e., those meeting stringent criteria 1 and 2). This, rather than using the total read count in the dataset, was done because the latter is contributed by both a background set of peaks as well as peaks from true bound locations. Since the former may vary independently of the latter, the read counts were normalized against the best estimate of true bound locations. The normalization value for each dataset was computed by dividing the median read counts for all peaks in all datasets that met stringent criteria 1 and 2 by the median read counts for all peaks in each dataset that met stringent criteria 1 and 2. The read count for all peaks in each dataset was then multiplied by its dataset-specific normalization value. The median read count across replicates was then determined for each CRC.

Criterion 3 involves motifs. MEME was used to identify over-represented DNA sequence recognition motifs located ±D/2 from each CRC for the set of consensus locations meeting relaxed criterion 1 and 2 (FIG. 4D and FIG. 9). The locations of these over-represented motifs were mapped throughout the genome. As a separate analysis, to assess the false positive rate, each sequence was scrambled multiple times and mapped. Those consensus binding locations that were $\leq$D/2+L by (20 by for Reb1) from a "very highly" or a "highly" over-representative motif midpoint were marked as meeting stringent and relaxed criteria 3, respectively (Table 5), where "L" denotes the length of the motif in bp.

Criterion 4 involves motif distance. When mapping at single base accuracy, how far a CRC is from a motif will depend on which coordinate in the motif is used as the frame of reference and which strand the motif resides. A strand-specific Motif Reference Coordinate (MRC) was therefore assigned that resided at a fixed position within the motif sequence (e.g., position 4 in TTACCCG), such that its distance to the CRC is minimized (FIG. 4E).

Since it was unknown a priori which position in the motif would provide the optimal MRC, the absolute distance (R) from each CRC to the closest Motif Start Coordinate (MSC) was calculated for each CRC meeting stringent criteria 1, 2, and 3. For this purpose, a motif located on the W strand has its MSC at its lowest coordinate ($W_{start}$), whereas a motif located on the C strand has its MSC at its highest coordinate ($C_{end}$). The MRC was then calculated to be: MRC=MSC+$R_{mode}$ for W strand motifs, and MRC=MSC-$R_{mode}$ for C strand motifs. The absolute nearest-integer distance between each CRC and its nearest MRC was calculated, and marked as meeting stringent or relaxed criteria 4 as indicated in Table 5.

Criterion 5 involves a read count. Median read counts per bound location for those CRC locations meeting stringent criterion 1-4 were binned (bin size=10), and plotted as a frequency distribution (FIG. 4F). Any CRC (regardless of stringency) having a read count that was >50% of the mode was marked as meeting stringent criterion 5, all other met relaxed criterion 5.

The following regions were not included in the main analyzed, but other regions of the genome (Telomere, tRNA genes, rDNA locus, and ARS elements) were considered and examined separately. These regions include: regions located within 15 kb of the end of a chromosomes (telomeric regions), since subtelomeric regions often have distinct type of factor binding than the rest of the genome; tRNA genes (from 150 by upstream of the TSS to the end of the gene); the rDNA locus (from 12:451000-469000); and ARS regions (defined by feature start/end coordinates).

The set of true bound locations were required to meet all five relaxed criteria listed in Table 5. These criteria were established by examining the subset of bound Reb1 locations meeting all stringent criteria except for the one being tested. The number of bound locations meeting the tested criteria at various cut-offs was then plotted. Points of obvious breaks in the trend were used to guide the definition of the stringent criteria. The relaxed criteria represent a nominal threshold.

While these criteria are designed to be generic, they may need to be altered for factors that lack one or more of the consensus properties listed in Table 5.

TABLE 4

Number of sequencing reads and barcode information

| | Replicate # | Reads[a] | Length[b] (bp) | Barcode | Barcode location |
|---|---|---|---|---|---|
| ChIP-seq | 1 | 2,938,677 | 35 | AGCG | P1 |
| ChIP-exo | 1 | 185,933 | 35 | GGAG | P1 |
| ChIP-exo | 2 | 902,048 | 35, 10* | GGGCTTNNNN** (SEQ ID NO: 1) | P2 |
| ChIP-exo | 3 | 1,515,889 | 35 | TCCC | P1 |
| ChIP-exo | 4 | 1,404,682 | 35 | TAGC | P1 |

[a] Number of uniquely aligned reads within 3 mismatches
[b] Length of sequencing read, including bar code
*Mate-paired sequencing
**NNNN for PCR bias check

TABLE 6

Number of true positives, false negatives, and false positives

| # stringent criteria | # relaxed criteria | True Positives | False Negatives | False Positives |
|---|---|---|---|---|
| 5 | 0 | 502 | 462 | 0 |
| 4 | 1 | 704 | 260 | 0 |
| 3 | 2 | 837 | 127 | 0.08 |
| 2 | 3 | 932 | 32 | 0.33 |
| 1 | 4 | 960 | 4 | 0.42 |
| 0 | 5 | 964 | 0 | 0.42 |

Example 7

Consumables for Preparing ChIP-Exo Libraries

| Product Name | Vendor |
|---|---|
| IgG sepharose (or Protein A sepharose) | Any Supplier Any Supplier |

TABLE 5

Criteria for establishing primary bound locations for regions of the genome associated with RNA polymerase II transcription[a]

| Name | Criteria | Stringent Rule | Stringent Reb1 | Relaxed Rule | Relaxed Reb1 | Notes |
|---|---|---|---|---|---|---|
| 0. Pre-filter | Read count per peak | n/a | n/a | Poisson distribution | $\geq 2, 7, 9, 9$ | For replicate sets 1-4, respectively |
| 1. Matched peak pairs | $\|C_{start} - W_{end}\|$ distance (bp) | $\leq 3\sigma_D$ | $\leq 5$ | $\leq D$ | $\leq 27$ | A matched pair comprises a W peak and an adjacent downtream C peak. |
| 2. Replicates | $\leq D/2$ bp apart | >70% | $\geq 3$ out of 4 | $\geq 50\%$ | $\geq 2$ out of 4 | A replicate must be $\leq D/2$ bp from another replicate. |
| 3. Motif | Degree of over-representation among all bound locations. | Very high | TTACCCK | High | NTACCCG TNACCCG TTACCCN TTGCCCG | A motif must be $\leq D/2 + L$ from a consensus location. |
| 4. Motif distance | Motif distance (bp) | $\leq 3\sigma_D$ | $\leq 5$ | $\leq D/2 + L^b$ | $\leq 20$ | Median distance to motif reference point (for all replicates) |
| 5. Read count | Per peak pair | >0.5(mode) | $\geq 43$ | Pre-filtered | $\geq 13$ | Minimal median read count per peak pair |

[a] The listed criteria was applied to those region that lie outside of tRNA genes, rDNA, ARS regions, and telomeric regions
[b] This distance represents a nominal maximum allowable distance since bound locations are expected to be considerably closer. L = length of DNA motif.

-continued

| Product Name | Vendor |
| --- | --- |
| (or Magentic beads) | Any Supplier |
| Antibody for a protein of interest | Any Supplier |
| (for Protein A sepharose or magnetic beads) | |
| Agencourt AMPure kit | Agencourt (Beckman Coulter Genomics, Danvers, MA) |
| Taq DNA polymerase enzyme | Any Supplier |
| 10X Taq DNA polymerase buffer | Any Supplier |
| dNTP PCR Mix (25 mM) | Any Supplier |
| Complete Protease Inhibitor Cocktail | Any Supplier |
| Phenol:chloroform:isoamyl alcohol 25:24:1 (25 ml) | Any Supplier |
| Glycogen (20 mg/mL) | Any Supplier |
| 100% Ethanol (50 ml) | Any Supplier |
| 70% Ethanol (25 ml) | Any Supplier |
| Gel Loading Solution | Any Supplier |
| Ethydium Bromide | Any Supplier |
| MinElute Gel Extraction Kit | Qiagen Inc. (Valencia, CA) |
| Isopropanol (25 ml) | Any Supplier |
| 0.5 mm Zirconia beads | Any Supplier |
| 22G Needle | Any Supplier |
| 10 mL Glass culture tubes | Any Supplier |
| 1.5-mL LoBind tubes | Any Supplier |
| 15-mL Conical polypropylene tubes | Any Supplier |

Example 8

Equipments for Preparing ChIP-Exo Libraries

| Product Name | Vendor |
| --- | --- |
| Bead beater | Any Supplier |
| Sonicator | Any Supplier |

-continued

| Product Name | Vendor |
| --- | --- |
| Microcentrifuge, refrigerated | Any Supplier |
| SpeedVac | Any Supplier |
| 6 Tube Magnetic Stand | Any Supplier |
| PCR machine | Any Supplier |
| Incubator (65 C.) | Any Supplier |
| ThermoMixer | Any Supplier |

Other Embodiments

Any improvement may be made in part or all of the systems, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. Although the experiments described herein involve transcription factors, the genomic location of any protein can be determined using the methods, kits and systems described herein. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of identifying a plurality of locations which a protein of interest binds to in a genome, the method comprising the steps of:
   (a) subjecting a plurality of cells or extract thereof to a chromatin immunoprecipitation assay using one or more antibodies that specifically bind to a protein of interest and resulting in double-stranded nucleic acid fragments bound to the protein of interest;
   (b) subjecting the double-stranded nucleic acid fragments bound to the protein of interest to exonuclease treatment and resulting in single-stranded nucleic acid fragments containing the plurality of locations which the protein of interest binds to, wherein each of the single-stranded nucleic acid fragments has an exonuclease-treated end sequence and the exonuclease treatment is carried out using a double-stranded nucleic acid-specific exonuclease that degrades a nucleic acid in only a 5'-to-3' or only a 3'-to-5' direction and a single-stranded nucleic acid-specific exonuclease that degrades a nucleic acid in the same direction as the double-stranded nucleic acid-specific exonuclease;
   (c) converting the single-stranded nucleic acid fragments to double-stranded nucleic acid fragments having exonuclease-treated end sequences;
   (d) identifying the exonuclease-treated end sequences; and
   (e) mapping the plurality of locations which the protein of interest binds to in the genome by identifying the exonuclease-treated end sequences.

2. The method of claim 1, wherein said identifying the exonuclease-treated end sequences comprises sequencing the double-stranded nucleic acid fragments having exonuclease-treated end sequences.

3. The method of claim 2, wherein the plurality of locations comprise a majority of locations which the protein of interest binds to.

4. The method of claim 1, wherein the protein of interest is a protein that binds directly or indirectly to the genome.

5. The method of claim 1, wherein said identifying the exonuclease-treated end sequences comprises performing at least one method selected from the group consisting of: deoxyribonucleic acid (DNA) sequencing, microarray assay, and polymerase chain reaction (PCR).

6. The method of claim 1, wherein the genome is selected from the group consisting of: eukaryotic genome, bacterial genome, and viral genome.

7. The method of claim 1, wherein the single-stranded nucleic acid-specific exonuclease is recJ and the double-stranded nucleic acid-specific exonuclease is lambda exonuclease.

8. The method of claim 1, wherein each of the plurality of locations is mapped within a resolution of five base pair or less.

9. The method of claim 1, wherein the genome is a human genome.

10. A method for identifying the nucleotides of a double-stranded nucleic acid sequence to which a peptide or a polypeptide binds, the method comprising the steps of:
   (a) obtaining a sample comprising a double-stranded nucleic acid sequence and a peptide or polypeptide;
   (b) binding the double-stranded nucleic acid sequence to the peptide or polypeptide, fragmenting the double-stranded nucleic acid sequence and resulting in double-stranded nucleic acid fragments having the peptide or polypeptide bound thereto;
   (c) immunoprecipitating the double-stranded nucleic acid fragments using one or more antibodies that specifically bind to the peptide or polypeptide, wherein the double-stranded nucleic acid fragments comprise flanking ends which are capable of being cleaved by exonucleases;
   (d) subjecting the double-stranded nucleic acid fragments from step (c) to exonuclease treatment, wherein the exonuclease treatment is carried out using a double-stranded nucleic acid-specific exonuclease that degrades a nucleic acid in only a 5'-to-3' or only a 3'-to-5' direction and a single-stranded nucleic acid-specific exonuclease that degrades a nucleic acid in the same direction as the double-stranded nucleic acid-specific exonuclease, and resulting in single-stranded fragment nucleic acid fragments, wherein each of the single-stranded nucleic acid fragments comprises nucleotides that bind to the peptide or polypeptide; and (e) identifying the nucleotides of the double-stranded nucleic acid sequence to which the peptide or a polypeptide binds by identifying the nucleotides that bind to the peptide or polypeptide in the single-stranded nucleic acid fragments.

11. The method of claim 10, wherein said identifying the nucleotides that bind to the peptide or polypeptide in the single-stranded nucleic acid fragments further comprises converting the single-stranded nucleic acid fragments to double-stranded nucleic acid fragments comprising nucleotides that bind to the peptide or polypeptide and sequencing the double-stranded nucleic acid fragments comprising nucleotides that bind to the peptide or polypeptide.

12. The method of claim 10, wherein the double-stranded nucleic acid sequence is a human genome.

13. The method of claim 10, wherein the double-stranded nucleic acid-specific exonuclease is lambda exonuclease.

14. The method of claim 12, further comprising mapping a location of the double-stranded nucleic acid sequence to which the peptide or polypeptide binds, and wherein the location is identified with a resolution of five base pairs or less.

15. A method of identifying a plurality of locations which a protein of interest binds to in a genome, the method comprising the steps of:

(a) subjecting a plurality of cells or extract thereof to a chromatin immunoprecipitation assay using one or more antibodies that specifically bind to a protein of interest and resulting in single-stranded nucleic acid fragments bound to the protein of interest;

(b) subjecting the single-stranded nucleic acid fragments bound to the protein of interest to exonuclease treatment and resulting in single-stranded nucleic acid fragments containing the plurality of locations which the protein of interest binds to, wherein each of the single-stranded nucleic acid fragments has an exonuclease-treated end sequence and the exonuclease treatment is carried out using a single-stranded nucleic acid-specific exonuclease that degrades a nucleic acid in only a 5'-to-3' or only a 3'-to-5' direction;

(c) converting the single-stranded nucleic acid fragments to double-stranded nucleic acid fragments having exonuclease-treated end sequences;

(d) identifying the exonuclease-treated end sequences; and (e) mapping the plurality of locations which the protein of interest binds to in the genome by identifying the exonuclease-treated end sequences.

16. The method of claim 15, wherein said identifying the exonuclease-treated end sequences comprises sequencing the double-stranded nucleic acid fragments having exonuclease-treated end sequences.

17. The method of claim 15, wherein the protein of interest is a protein that binds directly or indirectly to the genome.

18. The method of claim 15, wherein said identifying the exonuclease-treated end sequences comprises performing at least one method selected from the group consisting of: nucleic acid sequencing, microarray assay, and PCR.

19. The method of claim 15, wherein the genome is selected from the group consisting of: eukaryotic genome, bacterial genome, and viral genome.

20. The method of claim 15, wherein the single-stranded nucleic acid fragments are ribonucleic acid (RNA).

21. A method for identifying the nucleotides of a single-stranded nucleic acid sequence to which a peptide or a polypeptide binds, the method comprising the steps of:

(a) obtaining a sample comprising a single-stranded nucleic acid sequence and a peptide or polypeptide;

(b) binding the single-stranded nucleic acid sequence to the peptide or polypeptide, fragmenting the single-stranded nucleic acid sequence and resulting in single-stranded nucleic acid fragments having the peptide or polypeptide bound thereto;

(c) immunoprecipitating the single-stranded nucleic acid fragments using one or more antibodies that specifically bind to the peptide or polypeptide, wherein the single-stranded nucleic acid fragments comprise flanking ends which are capable of being cleaved by single-stranded nucleic acid exonucleases;

(d) subjecting the single-stranded nucleic acid fragments to exonuclease treatment, wherein the exonuclease treatment is carried out using a single-stranded nucleic acid-specific exonuclease that degrades a nucleic acid in only a 5'-to-3' or only a 3'-to-5' direction;

(e) reversing the binding of the peptide or polypeptide to the single-stranded nucleic acid fragments and converting the single-stranded nucleic acid fragments to double-stranded nucleic acid fragments comprising nucleotides that bind to the peptide or polypeptide; and (f) identifying the nucleotides of the single-stranded nucleic acid sequence to which the peptide or a polypeptide binds by identifying the nucleotides that bind to the peptide or polypeptide in the double-stranded nucleic acid fragments.

22. The method of claim 21, wherein the single-stranded nucleic acid sequence is RNA.

23. The method of claim 21, wherein said identifying the nucleotides that bind to the peptide or polypeptide in the double-stranded nucleic acid fragments comprises sequencing the double-stranded nucleic acid fragments.

* * * * *

SEQUENCE LISTING

```
<160> NUMBER OF SEQ ID NOS: 16

<210> SEQ ID NO 1
<211> LENGTH: 10
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(10)
<223> OTHER INFORMATION: n is a, c, g, or t

<400> SEQUENCE: 1 gggcttnnnn                                                        10

<210> SEQ ID NO 2
<211> LENGTH: 10
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(10)
<223> OTHER INFORMATION: n is a, c, g, or t

<400> SEQUENCE: 2
```

-continued

```
acggagnnnn                                                          10

<210> SEQ ID NO 3
<211> LENGTH: 10
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(10)
<223> OTHER INFORMATION: n is a, c, g, or t

<400> SEQUENCE: 3 agcgttnnnn                                                          10

<210> SEQ ID NO 4
<211> LENGTH: 10
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(10)
<223> OTHER INFORMATION: n is a, c, g, or t

<400> SEQUENCE: 4 cgggtcnnnn                                                          10

<210> SEQ ID NO 5
<211> LENGTH: 11
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 5
agagaatgag g                                                        11

<210> SEQ ID NO 6
<211> LENGTH: 25
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 6
aactgccccg ggttcctcat tctct                                         25

<210> SEQ ID NO 7
<211> LENGTH: 54
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (26)..(29)
<223> OTHER INFORMATION: n is a, c, g, or t

<400> SEQUENCE: 7
cgccttggcc gtacagcagg ggcttnnnna gagaatgagg aacccggggc agtt         54

<210> SEQ ID NO 8
<211> LENGTH: 52
<212> TYPE: DNA
<213> ORGANISM: ARTIFICIAL SEQUENCE
```

```
<220> FEATURE:
<223> OTHER INFORMATION: SYNTHETIC CONSTRUCT
<220> FEATURE:
<221> NAME/KEY: misc_feature
<222> LOCATION: (24)..(27)
<223> OTHER INFORMATION: n is a, c, g, or t

<400> SEQUENCE: 8
ctgccccggg ttcctcattc tctnnnnaag ccctgctgt acggccaagg cg         52

<210> SEQ ID NO 9
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 9
ctgccccggg ttcctcattc tct                                         23

<210> SEQ ID NO 10
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 10
tctctatggg cagtcggtga t                                           21

<210> SEQ ID NO 11
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 11
atcaccgact gcccatagag agg                                         23

<210> SEQ ID NO 12
<211> LENGTH: 25
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12
tctctatggg cagtcggtga tagcg                                       25

<210> SEQ ID NO 13
<211> LENGTH: 27
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 13
cgctatcacc gactgcccat agagagg                                     27

<210> SEQ ID NO 14
<211> LENGTH: 41
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14
```

```
ccactacgcc tccgctttcc tctctatggg cagtcggtga t                41

<210> SEQ ID NO 15
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 15
ctgccccggg ttcctcattc t                                     21

<210> SEQ ID NO 16
<211> LENGTH: 10
<212> TYPE: DNA
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: misc_feature
<222> LOCATION: (7)..(10)
<223> OTHER INFORMATION: n is a, c, g, or t

<400> SEQUENCE: 16 tagcgtnnnn                                                  10
```